(12) United States Patent
Hara et al.

(10) Patent No.: US 6,590,710 B2
(45) Date of Patent: Jul. 8, 2003

(54) FABRY-PEROT FILTER, WAVELENGTH-SELECTIVE INFRARED DETECTOR AND INFRARED GAS ANALYZER USING THE FILTER AND DETECTOR

(75) Inventors: Hitosh Hara, Tokyo (JP); Naoki Kishi, Tokyo (JP); Makoto Noro, Tokyo (JP); Hideto Iwaoka, Tokyo (JP); Kentaro Suzuki, Tokyo (JP)

(73) Assignee: Yokogawa Electric Corporation, Musashino (JP)

( * ) Notice: Subject to any disclaimer, the term of this patent is extended or adjusted under 35 U.S.C. 154(b) by 0 days.

(21) Appl. No.: 09/777,901

(22) Filed: Feb. 5, 2001

(65) Prior Publication Data

US 2002/0003663 A1 Jan. 10, 2002

(30) Foreign Application Priority Data

| Feb. 18, 2000 | (JP) | 2000-041287 |
|---|---|---|
| Feb. 18, 2000 | (JP) | 2000-041288 |
| Dec. 6, 2000 | (JP) | 2000-371261 |

(51) Int. Cl.$^7$ ............................................. G02B 27/00
(52) U.S. Cl. ....................... 359/579; 359/578; 359/586; 359/589; 356/454; 356/519
(58) Field of Search ........................ 359/579, 578, 359/580, 584, 585, 586, 589, 260, 261; 372/92, 99; 356/450, 454, 519

(56) References Cited

U.S. PATENT DOCUMENTS

| 5,040,895 A | 8/1991 | Laurent et al. ............. 356/454 |
| 5,142,414 A | 8/1992 | Koehler ....................... 359/578 |
| 5,218,422 A | 6/1993 | Zoechbauer ................. 356/454 |
| 5,225,888 A | 7/1993 | Selwyn ........................ 356/454 |
| 5,646,729 A | 7/1997 | Koskinen ..................... 356/454 |
| 5,818,586 A | 10/1998 | Lehto ........................... 356/454 |
| 5,831,262 A * | 11/1998 | Greywall et al. ........ 250/227.14 |
| 2002/0031155 A1 * | 3/2002 | Tayebati et al. .............. 372/50 |

OTHER PUBLICATIONS

O. S. Heavens, "Optical Properties of Thin Solid Films", Dover Publications, New York, 1991, pp. 215–221.*

F. L. Pedrotti, L. S. Pedrotti, "Introduction to Optics", Prentice Hall, New Jersey, 1993, pp. 391–398.*

* cited by examiner

Primary Examiner—Thong Nguyen
Assistant Examiner—Arnel C. Lavarias

(57) ABSTRACT

A Fabry-Perot filter device for selectively transmitting three wavelength bands of infrared radiation, including a reference light band, wherein the filter device comprises a fixed mirror formed on a substrate; a movable mirror arranged opposite to the fixed mirror with a gap formed therebetween so that the movable mirror is displaced with respect to the fixed mirror by applying an external force; a fixed electrode formed on the fixed mirror; and a movable electrode formed on the movable mirror and arranged opposite to the fixed electrode wherein the movable electrode is displaced by applying a potential difference across the fixed and movable electrodes so that the width of the gap is varied in at least three steps, whereby at least three wavelength bands of infrared radiation are selectively transmitted through the filter device.

12 Claims, 13 Drawing Sheets

FIG.21
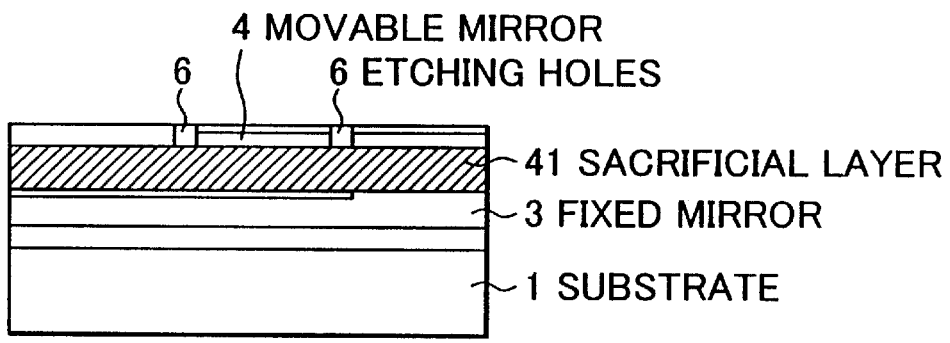
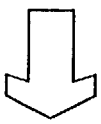
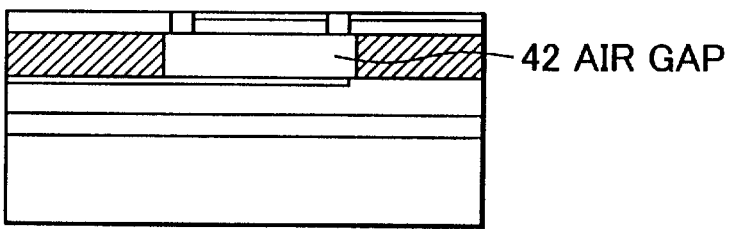
FIG.22
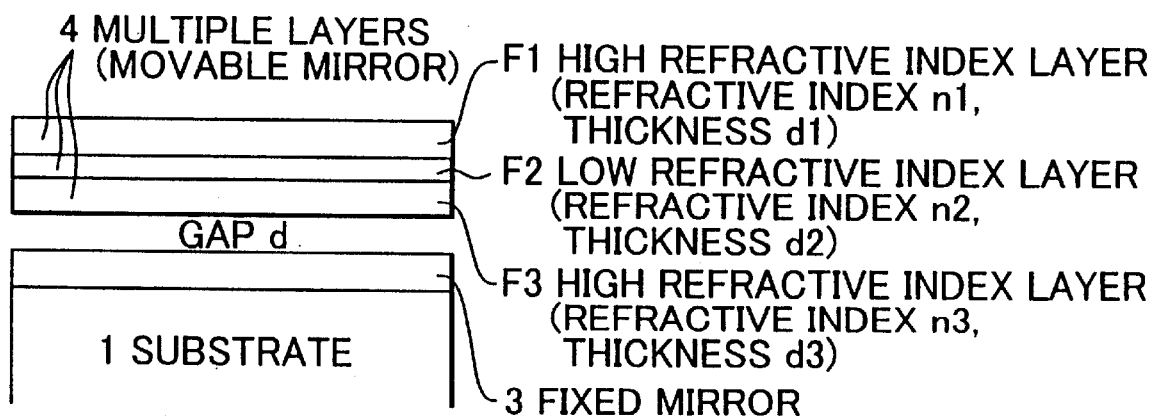

AIR/POLYSi/SiN/POLYSi/AIR/POLYSi/SiO2/Si SUBSTRATE/SiO2/AIR

AIR/POLYSi/AIR/POLYSi/SiO2/Si SUBSTRATE/SiO2/AIR

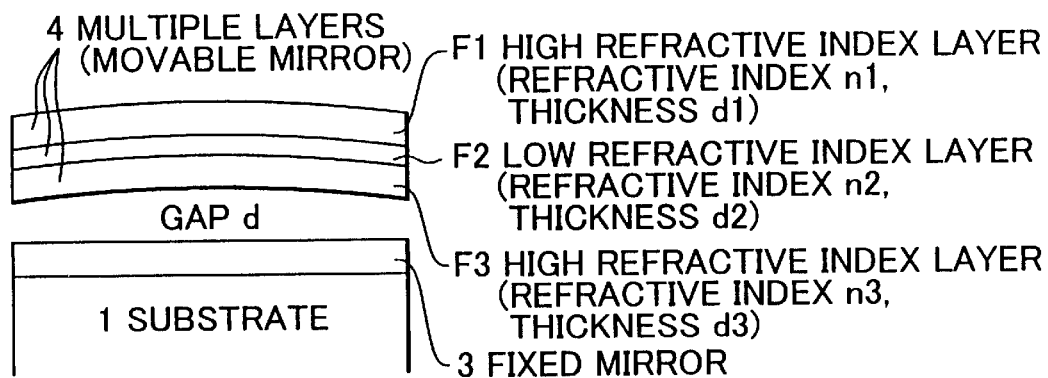
FIG.26
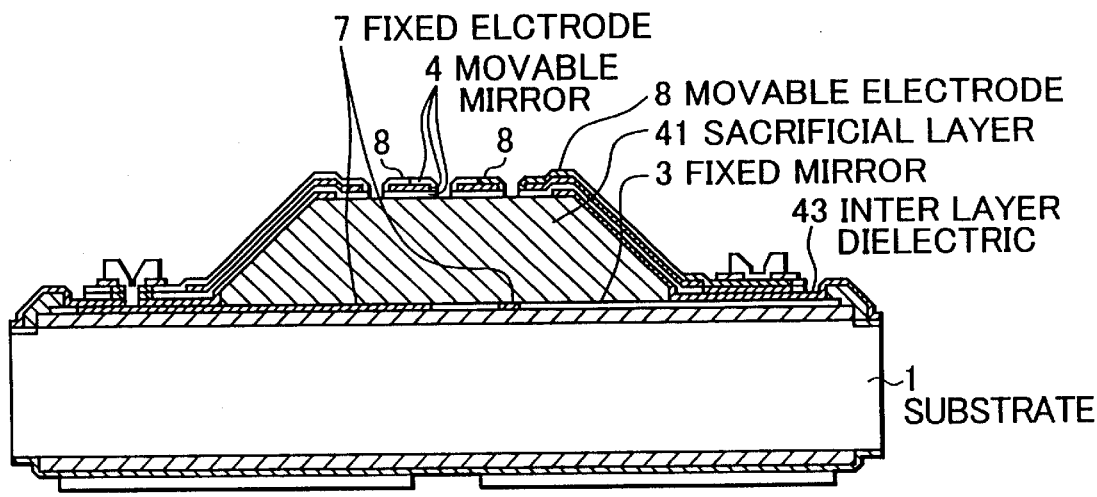
FIG.27A  BEFORE SACRIFICIAL ETCHING
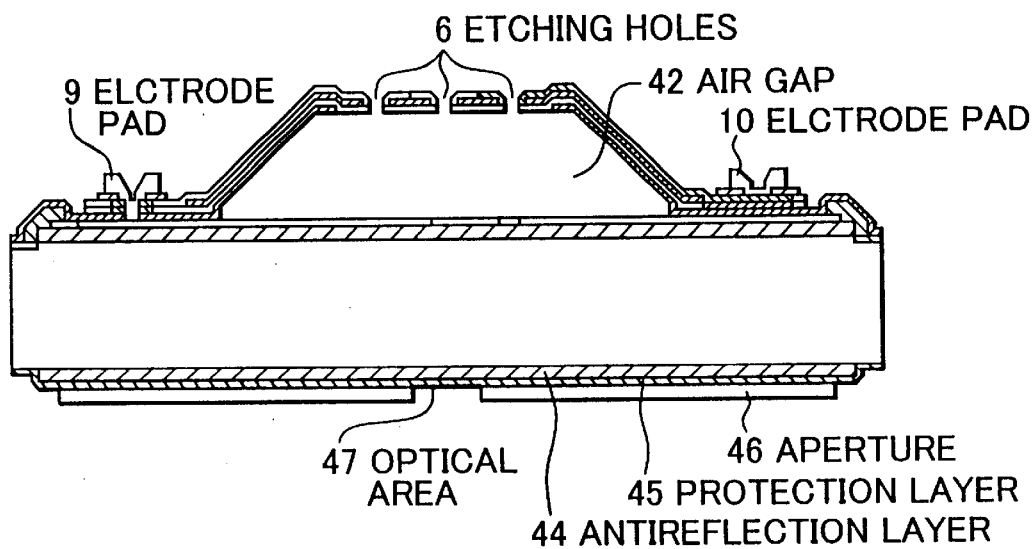
FIG.27B  AFTER SACRIFICIAL ETCHING

FABRY-PEROT FILTER, WAVELENGTH-SELECTIVE INFRARED DETECTOR AND INFRARED GAS ANALYZER USING THE FILTER AND DETECTOR

BACKGROUND OF THE INVENTION

1. Field of Invention

This invention relates to a Fabry-Perot filter device used as a wavelength selective filter for transmitting rays of light, such as infrared radiation, in a wavelength selective manner; a wavelength selective infrared detector comprising the Fabry-Perot filter device and an infrared detector; and a non-dispersive infrared gas analyzer for measuring concentration of a gas or gases by detecting infrared radiation transmitted through the Fabry-Perot filter device.

2. Description of the Prior Art

A non-dispersive infrared gas analyzer, hereinafter called "NDIR gas analyzer", is used to analyze a gas, wherein the analyzer detects the amount of infrared absorption to measure the concentration of the gas, utilizing the principle that the wavelength bands of infrared radiation to be absorbed depends on the type of gas.

FIGS. 1 to 5 show examples of prior art NDIR gas analyzers. In the following, the gas being measured is assumed to be carbon dioxide whose peak wavelength of infrared radiation absorption is approximately 4.25 $\mu$m.

FIG. 1 shows a single ray, one wavelength NDIR gas analyzer comprising a sample cell 110, whereinto a gas is supplied; a light source 111; a filter 112; and an infrared detector 113. In this example, filter 112 is tuned to the absorption bands of carbon dioxide shown in FIG. 6 to select and pass a band of infrared radiation having wavelengths in the vicinity of 4.25 $\mu$m. Infrared detector 113 determines the concentration of the gas being measured by detecting infrared radiation transmitted through filter 112.

FIG. 2 shows a single ray two wavelength comparative NDIR gas analyzer, wherein the analyzer selects two wavelength bands using filter 112, tuned to the absorption band of carbon dioxide, and a filter 114 for transmitting an infrared radiation band of wavelengths in the vicinity of approximately 3.9 $\mu$m, as a reference light. The bands of infrared radiation thus selected are detected respectively with infrared detectors 113 and 115. In this example, it is possible to correct a change in the output signal with time due to, for example, deterioration in light source 111 or contamination in sample cell 110 by comparing the carbon dioxide absorption band with the measured absorption band of the reference light.

FIG. 3 shows another single ray two wavelength comparative NDIR gas analyzer, wherein the analyzer selects two wavelength bands using filter 112 formed on a disc 116 and tuned to the absorption band of carbon dioxide and the filter 114 for reference light. The bands of infrared radiation selected by the filters as disc 116 is rotated are then detected with infrared detector 113. In this example, it is also possible to correct a change in the output signal with time due to, for example, deterioration in light source 111 or contamination in sample cell 110, by comparing the carbon dioxide absorption band with the measured absorption band of the reference light.

FIG. 4 shows a single ray two wavelength Fabry-Perot NDIR gas analyzer, wherein a gap between two parallel mirrors, comprising a Fabry-Perot filter 117, is made variable so that two bands are selected, one being a band tuned to the absorption band of the gas being measured and the other being a band of reference light. The bands of infrared radiation thus selected are respectively detected with infrared detector 113. In this example, it is also possible to correct a change in the output signal with time due to, for example, deterioration in light source 111 or contamination in sample cell 110, by comparing the carbon dioxide absorption band with the measured absorption band of the reference light.

As shown in FIG. 8, the Fabry-Perot filter is an optical filter using a device (e.g. Fabry-Perot plates) wherein a pair of high reflectance mirrors 120 and 121 are placed in parallel and opposite to each other with a gap formed therebetween. Assuming that the width (i.e. distance between) of the gap in the Fabry-Perot filter is "d" and the refractive index within the gap is "n", then the rays, among the rays of incident light, that satisfy the phase relationship represented by below equation (1) will enhance each other by interference, thus becoming transmitted light. In equation (1), $\delta$ is the phase reference, $\phi$ is the angle of light incident on the device, and $\lambda$ is the wavelength of the light. FIG. 9 shows how the rays are transmitted.

$$\delta = 4\pi nd \cos\phi/\lambda \tag{1}$$

The Fabry-Perot filter is designed so that the wavelength bands of the transmitted light passing through the device can be varied by making the gap width "d" variable. An example of a variable wavelength Fabry-Perot filter comprises a fixed mirror, and a movable mirror arranged opposite to the fixed mirror with a gap formed therebetween, with a fixed electrode on the fixed mirror and a movable electrode on the movable mirror, and means are provided for applying a voltage to the electrodes so that the movable mirror is moved accordingly and the gap is thereby adjusted in width. For example, such a Fabry-Perot filter can be used as a wavelength selective filter for a non-dispersive infrared carbon dioxide sensor and selectively pass the wavelength band of carbon dioxide absorption, of approximately 4.25 $\mu$m, and the wavelength band of reference light, of approximately 3.9 $\mu$m.

FIG. 5 shows a double ray, one wavelength NDIR gas analyzer, wherein two light sources 111 and 118 are arranged so that the optical paths thereof differ from each other within sample cell 110. In this example, a change in the output signal with time due to, for example, contamination of sample cell 110 is corrected according to the ratio between two output signals of infrared detector 113 provided by a band of infrared radiation that is transmitted through filter 112 tuned to the absorption band of the gas being measured. The concentration of the gas being measured is then determined.

In the foregoing type of NDIR gas analyzer, however, the number of filters must be increased to be able to measure concentrations of a plurality of gases or a plurality of constituents of a gas. Hence, the prior art gas analyzers all have such problems as high cost and large sizes.

SUMMARY OF THE INVENTION

Accordingly, an object of the invention is to overcome the aforementioned and other problems, deficiencies and disadvantages of the prior art.

Another object is to provide an infrared gas analyzer capable of simultaneously determining concentrations of at least two constituents of a gas being measured by using a Fabry-Perot filter device for selectively transmitting at least three wavelength bands of infrared radiation which includes a reference light.

The foregoing and other objects are attained in the invention which encompasses a Fabry-Perot filter device for passing infrared radiation from a light source in a wavelength selective manner, and comprising a fixed mirror formed on a substrate; a movable mirror arranged opposite to the fixed mirror with a gap formed therebetween so that the movable mirror is displaced with respect to the fixed mirror by applying an external force; a fixed electrode formed on the fixed mirror; and a movable electrode formed on the movable mirror and arranged opposite to the fixed electrode; wherein the movable mirror is displaced by applying a potential difference across the fixed and movable electrodes so that the width of the gap is varied in at least three steps, whereby at least three wavelength bands of the infrared radiation are selectively transmitted through the filter device.

A feature of the invention is the fixed mirror and the movable mirror both comprising silicon.

Another feature is the fixed electrode and the movable electrode both comprise silicon with a high impurity concentration.

Another aspect of the invention is an infrared gas analyzer for determining concentration of a gas being measured according to output of an infrared detector, end comprising a light source for emitting infrared radiation to the gas being measured; a wavelength selective filter for passing the infrared radiation from the light source in a wavelength selective manner; and an infrared detector for detecting infrared radiation passing through the wavelength selective filter, wherein the wavelength selective filter comprises the above referred to Fabry-Perot filter device.

Another feature of the invention is that the wavelength selective filter is disposed before the infrared detector in an optical path and comprises a wide bandpass filter for passing only a specific band of wavelengths.

A further aspect of the invention is a wavelength selective infrared detector comprising a substrate; a wavelength selective filter formed on the substrate for passing infrared radiation from a light source in a wavelength selective manner; and an infrared detector formed on the substrate for detecting infrared radiation passing through the wavelength selective filter.

A feature of the invention is that the infrared detector comprises elements located in a sealed cavity formed in the substrate, and wherein the wavelength selective filter is formed on the sealed cavity so that the sealed cavity is sealed with an inert gas therein.

A yet further aspect of the invention is a wavelength selective infrared detector comprising a wavelength selective filter formed on a first substrate to pass infrared radiation from a light source in a wavelength selective manner; and an infrared detector formed on a second substrate and comprising detector elements for detecting infrared radiation passing through the wavelength selective filter, wherein the first and second substrates are joined together.

A further feature is that in the just mentioned wavelength selective infrared detector, the infrared detector elements are located within a grooved shaped part formed in the second substrate so as to form a sealed cavity and the wavelength selective filter is positioned on the groove shaped part to form the sealed cavity, so that the sealed cavity has inert gas therein.

Another feature is that in the just mentioned wavelength selective infrared detector, the wavelength selective filter is a Fabry-Perot filter device comprising a fixed mirror located on a substrate and a movable mirror arranged opposite to the fixed mirror so that a gap is formed therebetween and the movable mirror is displaced with respect to the fixed mirror by applying an external force.

A further feature is that a fixed electrode is formed on the fixed mirror and a movable electrode is formed on the movable mirror and electric power is applied to the electrodes to cause the movable mirror to be displaced and the width of the gap to be varied.

Another feature is that the gap is varied by applying a plurality of voltages across the fixed electrode and movable electrodes so that a plurality of bands of wavelengths are passed by the filter device.

A yet further feature is that the infrared detector of the invention may comprise a bolometer.

A still further feature is a plurality of the wavelength selective filters and a plurality of infrared detectors arranged horizontally in arrays.

A further aspect of the invention is an infrared gas analyzer for determining concentration of a gas being measured according to output of an infrared detector, comprisng a light source for emitting infrared radiaton to the gas being measured; a wavelength selective filter for passing infrared radiation from the light source in a wavelength selective manner; and an infrared detector for detecting infrared radiation passing through the wavelength selective filter; wherein the wavelength selective filter is formed on a substrate, and the infrared detector is formed on the same substrate or the infrared detector is formed on a second substrate with the second substrate being joined to the first substrate.

A feature of the invention is a wide bandpass filter being disposed between the wavelength selective infrared detector and the light source so as to pass only a specific band of wavelength.

Another feature of the invention is that the gas being measured contains one component of carbon dioxide, and another component being water, or carbon monoxide, or nitrogen oxide, or sulfur oxide, and wherein concentrations thereof are measured.

A further feature is that the gas being measured is nitrogen oxide and sulfur oxide.

A further aspect of the invention comprises a Fabry-Perot filter device comprising a fixed mirror and a movable mirror with a gap formed therebetween, and wherein the movable mirror is formed of a multilayer optical thin film comprising at least one layer presenting tensile stress; or at least one layer presenting compressive stress, or at least two layers presenting different levels of tensile stress, or at least three layers comprising a high refractive index layer, a low refractive index layer, and another high refractive index layer, of different tensile and compressive stress.

A feature of the invention is that the thin film has a thickness of $\lambda/4$ wherein $\lambda$ is the wavelength.

Another feature is that an isolation layer is provided between a fixed electrode which is formed on the fixed mirror and a movable electrode which is formed on the movable mirror.

Another feature is that the isolation layer is formed on the fixed electrode and is made of silicon nitride or silicon oxide.

A further feature is that the fixed mirror is formed on a substrate, and the gap is formed by depositing a sacrificial layer of predetermined shape and size between the fixed mirror and the movable mirror and then removing the sacrificial layer completely or partially, such as by means of etching.

A yet further feature is that the artificial layer has a trapezoid shaped cross section and electrode pads are formed outside of said sacrificial layer.

Another feature is that an anti-refection layer is formed on a backside of a substrate, and a metal aperture is formed on the anti-reflection layer through a protection layer and having an optical area in part, wherein the sacrificial layer is first removed by etching and then a portion of the protection layer present in the optical area is removed.

A further feature is that etching holes are provided at a center and along a periphery of the movable mirror in order to etch the sacrificial layer.

BRIEF DESCRIPTION OF THE DRAWINGS

FIG. 21 is a cross-sectional view depicting formation of a gap in the Fabry-Perot filter.

FIG. 22 is a cross-sectional view depicting a Fabry-Perot filter device of the invention.

FIG. 26 is a schematic view depicting an example of a multilayer movable mirror.

FIGS. 27A and 27B are cross-sectional views depicting a second illustrative embodiment of a Fabry-Perot filter device of the invention.

DETAILED DESCRIPTION OF THE PREFERRED EMBODIMENTS

First Illustrative Embodiment of a Fabry-Perot Filter Device

Figure 1:
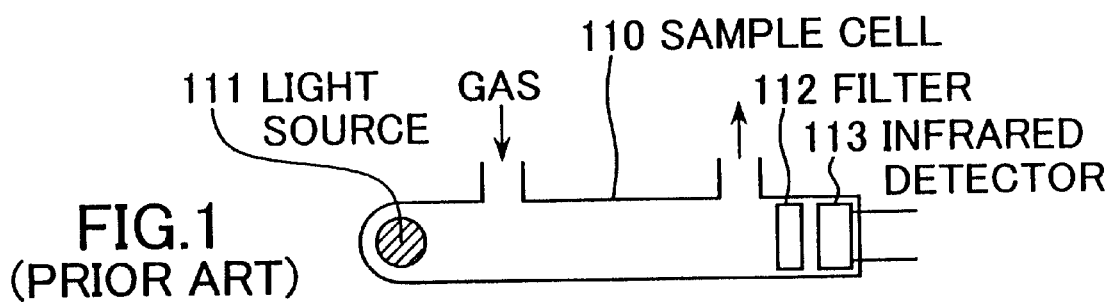
FIG. 1 is a schematic view depicting a prior art NDIR gas analyzer.
Figure 2:
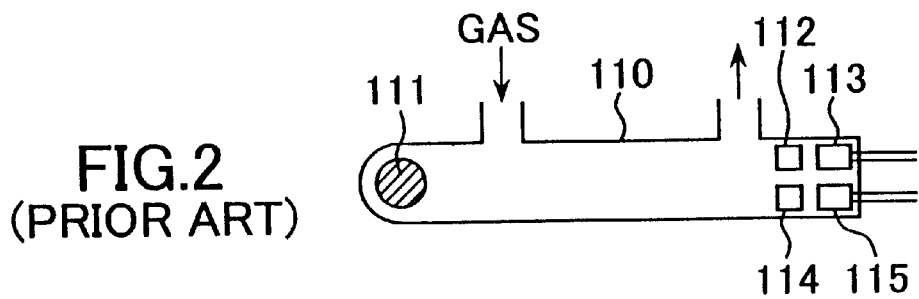
FIG. 2 is a schematic view depicting another prior art NDIR gas analyzer.
Figure 3:
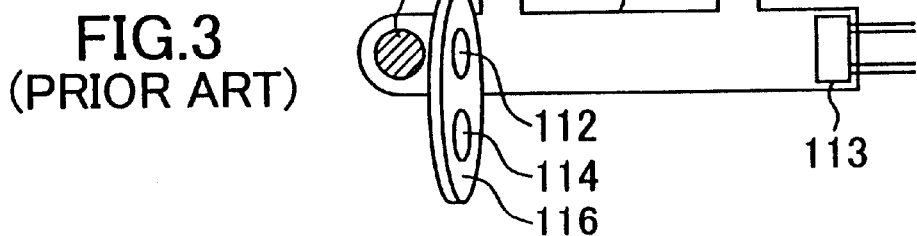
FIG. 3 is a schematic view depicting yet another prior art NDIR gas analyzer.
Figure 4:
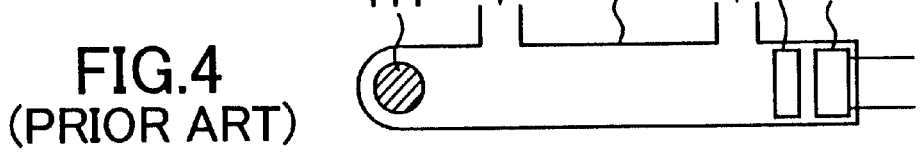
FIG. 4 is a schematic view depicting still another prior art NDIR gas analyzer.
Figure 5:
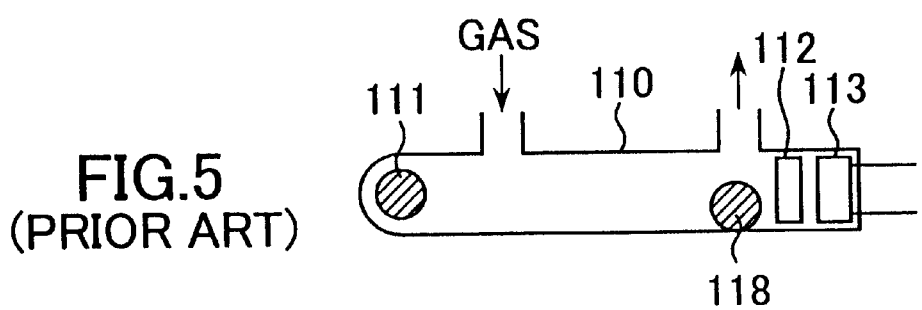
FIG. 5 is a schematic view depicting a further prior art NDIR gas analyzer.
Figure 6:
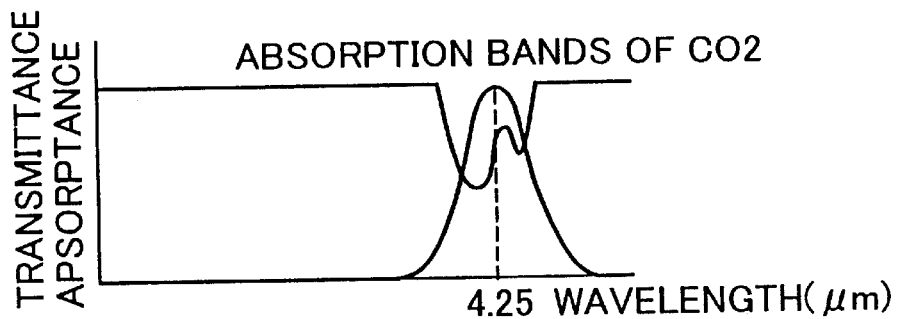
FIG. 6 is a graph depicting infrared transmission and absorption bands of a filter.
Figure 7:
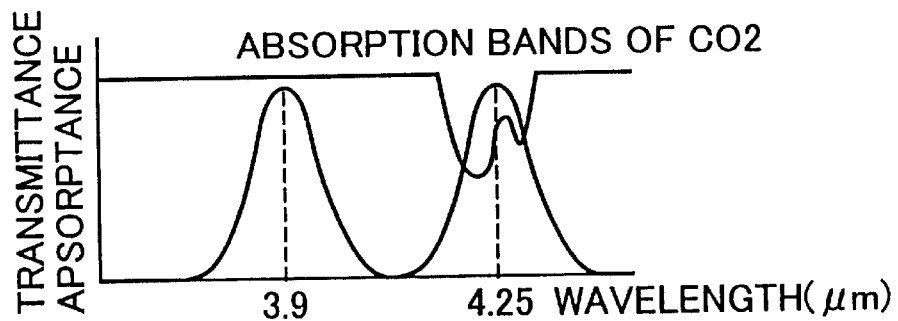
FIG. 7 is a graph depicting infrared transmission and absorption bands of another filter.
Figure 8:
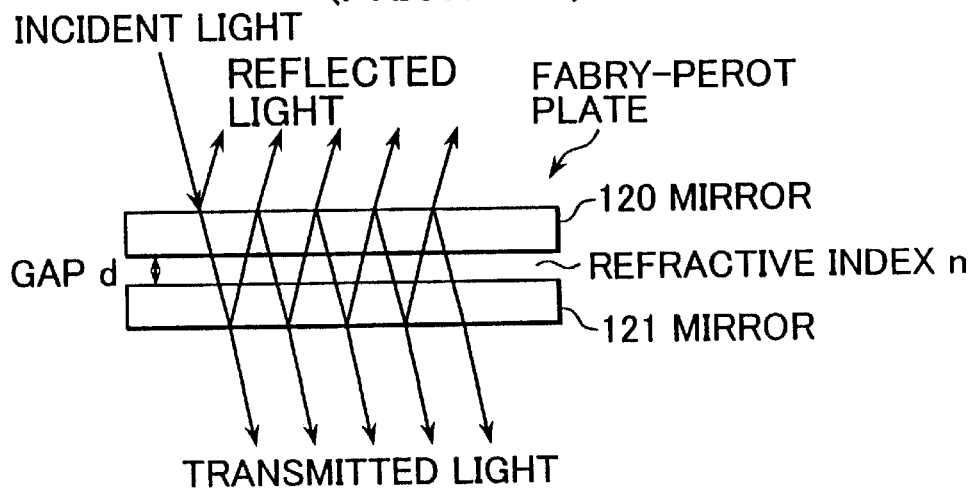
FIG. 8 is a schematic view explaining Fabry-Perot platee.
Figure 9:
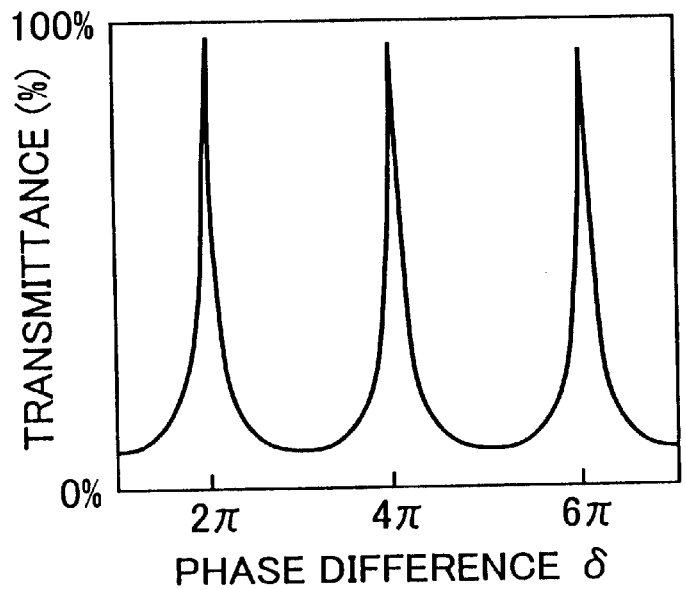
FIG. 9 is a graph depicting the way light is transmitted through a Fabry-Perot filter.
Figure 10:
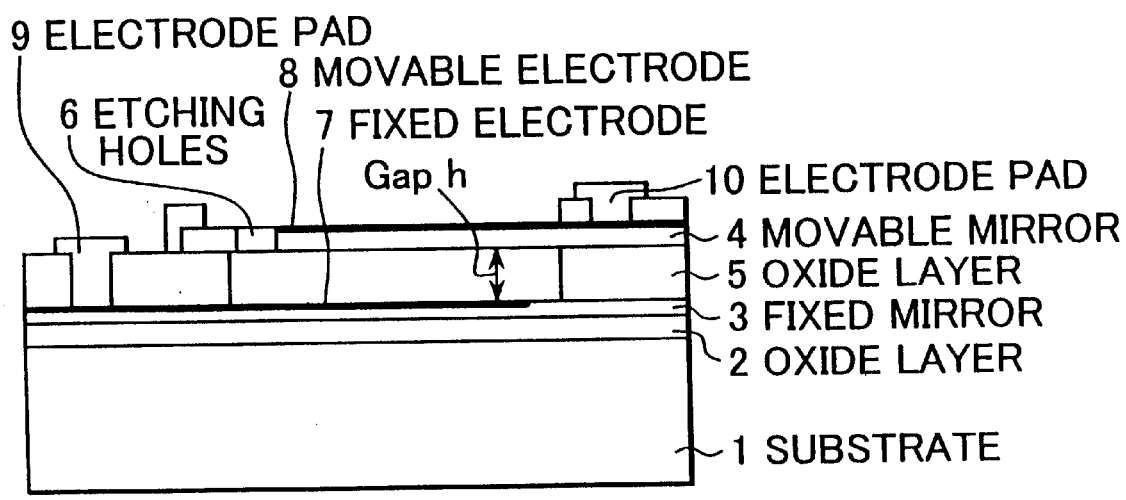
FIG. 10 is a cross-sectional view depicting a first illustrative embodiment of a Fabry-Perot filter device of the invention.
Figure 11:
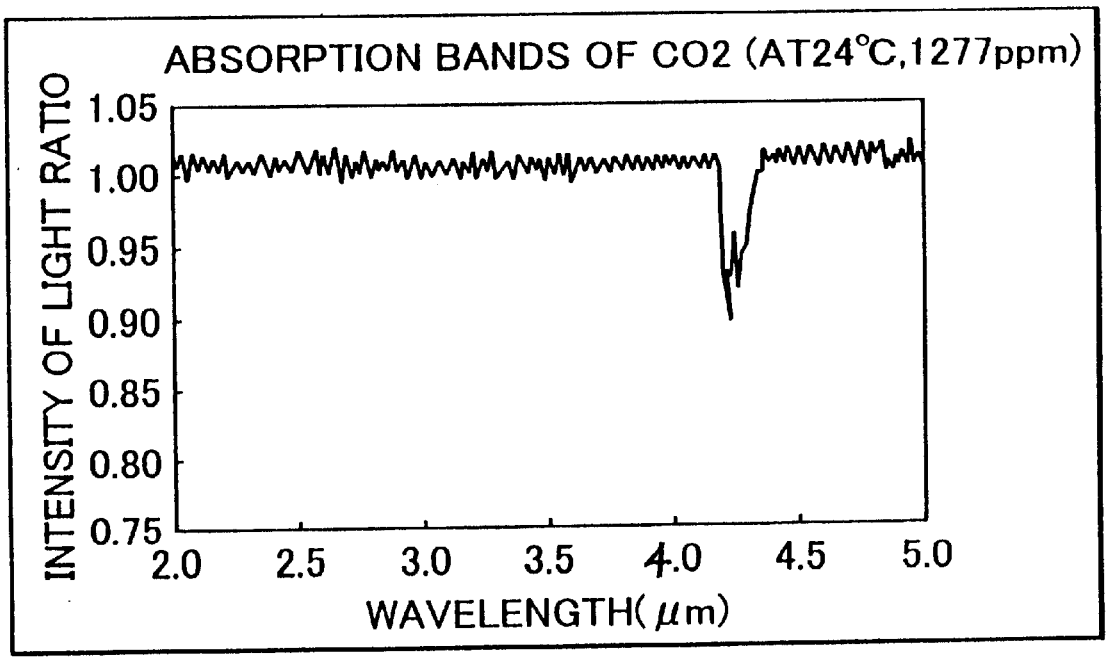
FIG. 11 is a graph depicting an infrared absorption band of carbon dioxide.
Figure 12:
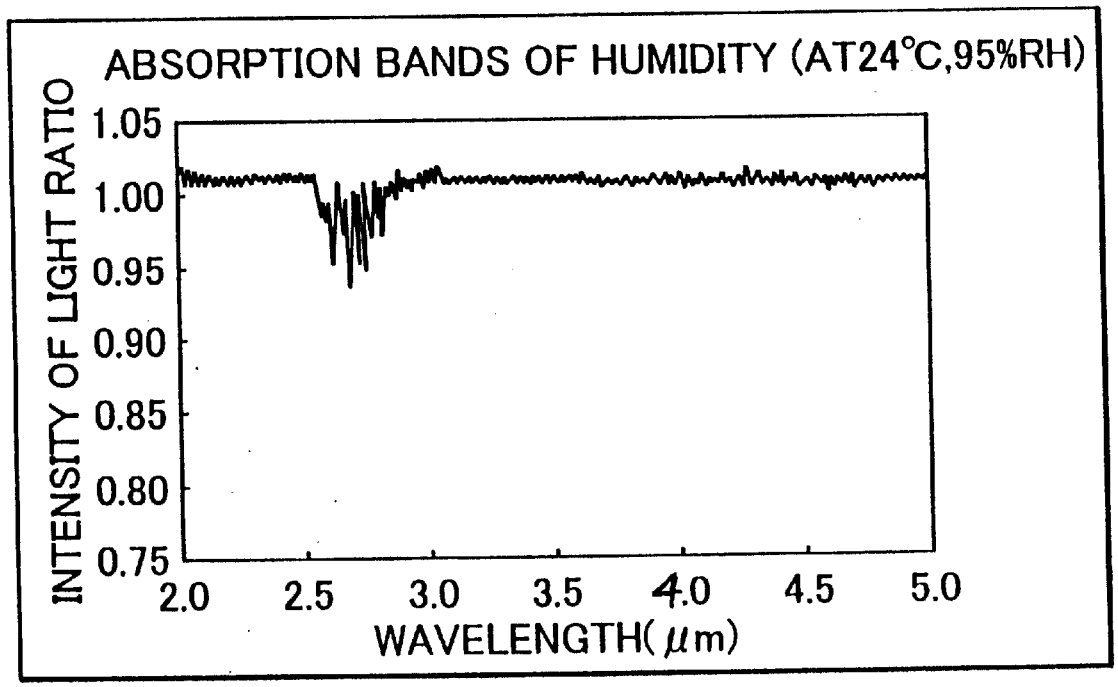
FIG. 12 is a graph depicting absorption band of water vapor.

Hereinafter, it is assumed that the gas being measured is a gas containing two components, one of which is carbon dioxide whose peak wavelength of infrared absorption is approximately 4.25 $\mu$m, as shown in FIG. 11, and the other is water vapor whose peak wavelength of infrared absorption is approximately 2.7 $\mu$m, as shown in FIG. 12. Of course, any other gas or gases can be measured with the invention. The Fabry-Perot filters are normally designed in such a manner that the central wavelength ranges from 2700 nm($\lambda$1) to 4250 nm ($\lambda$2) and and the free spectral range (FSR) is greater than 4250–2700 nm($\lambda$2–$\lambda$1)=1550 nm. The Fabry-Perot filter, as shown in FIG. 10, is designed so that the free spectral range FSR=2000 nm, half width HBW=140 nm, maximum transmittance Tmax=80%, and Finesse=14.

In FIG. 10, a fixed mirror 3 is formed on a silicon substrate 1 via an oxide layer 2, and a movable mirror 4 is formed on an oxide layer 5 deposited on fixed mirror 3 and arranged opposite to fixed mirror 3. A gap "h", equivalent to the thickness of oxide layer 5, is formed between fixed mirror 3 and movable mirror 4, by etching oxide layer 5, through etching holes 6 formed on movable mirror 4. Movable mirror 4 can be displaced toward fixed mirror 3 by applying an external force. Fixed mirror 3 and movable mirror 4 are made of, for example, polysilicon. A fixed electrode 7 is formed on fixed mirror 3 by doping the surface thereof with a high concentration impurity or impurities. Similarly, a movable electrode 8 is formed on movable mirror 4 by doping the surface thereof with a high concentration impurity or impurities. An electrode pad 9 is formed on fixed electrode 7 in contact therewith to enable the electrode to be supplied with external power. Similarly, an electrode pad 10 is formed on movable electrode 8 in contact therewith to enable electrode 8 to be supplied with external power.

The central wavelength $\lambda$ of the Fabry-Perot filter device is equivalent to the width or thickness of the gap "h", i.e. the thickness of oxide layer 5, and is 3100 nm, for example. Since fixed mirror 3 serves as the lower mirror of the Fabry-Perot filter, the optical film thickness of the mirror equals $\lambda/4$. In the embodiment, oxide layer 5 is 592 nm thick and has a refractive index of 1.309, and the layers of the fixed mirror 3 and movable mirror 4 are 248 nm thick and have a refractive index of 3.125.

The operation of the Fabry-Perot filter device is described with reference to FIGS. 13A–13C. Once a potential difference is applied across fixed electrode 7 and movable electrode 8 through pads 9 and 10, an electrostatic attraction force is produced between the fixed and movable electrodes. Thus, movable mirror 4 is displaced with respect to fixed mirror 3, thereby changing the width of gap "h". By varying the voltage, it is possible to determine the width of gap "h" at which infrared radiation with wavelength bands corresponding to the absorption bands of the gas being measured are transmitted through the Fabry-Perot filter device of the invention.

Figure 13A:
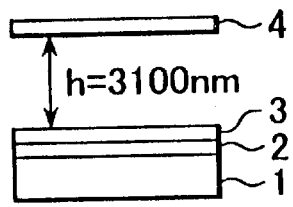
FIGS. 13A–13C are schematic views explaining behavior of the first illustrative embodiment of the Fabry-Perot filter device of the invention.

For example, assume that in FIG. 13A, the width of gap "h" (i.e. the thickness of an isolation layer of about 3100 nm) in the non-electrified, initial state of the Fabry-Perot filter is when a reference light is measured. Then, it is possible to use a change in the amount of transmitted light as data for correcting a change in the light source due to aging or contamination in the optical system.

Figure 13B:
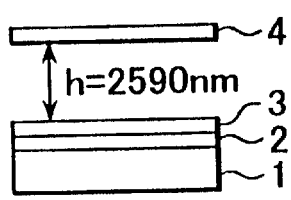
Figure 13C:
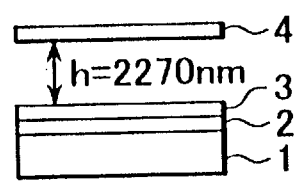

The object to be measured can be switched to water vapor by adjusting the potential difference, so that the gap "h" is approximately 2590 nm, as shown in FIG. 13B. Similarly, the object can be further switched to carbon dioxide by adjusting the potential difference so that the gap "h" is approximately 2270 nm, as shown in FIG. 13C. As described above, the gap "h" is made variable in three steps. Hence, it is possible to realize a Fabry-Perot filter device which selectively transmits at least three wavelength bands of infrared radiation, including a wavelength band of reference light.

Assuming that the Fabry-Perot filter device of the invention is used with an infrared gas analyzer comprising a light source for emitting infrared radiation to the gas being measured, a wavelength selective filter for transmitting the infrared radiation from the light source in a wavelength selective manner; and an infrered detector for detecting infrared radiation which is transmitted through the wavelength selective filter; in order to determine the concentration of the gas being measured according to the output of the infrared detector. Then, it is possible to simultaneously measure the concentrations of the two constituents of the gas or gases being measured, without having to increase the number of wavelength selective filters. Thus, it is possible to advantageously reduce the size and cost of an infrared gas analyzer.

Figure 14:
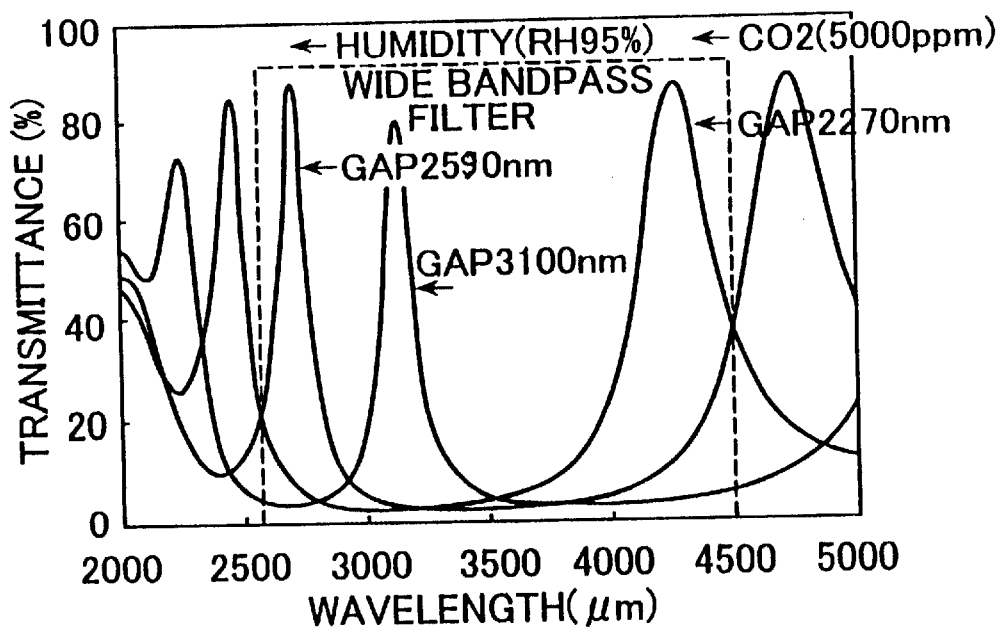
FIG. 14 is a graph depicting the transmission and gas absorption bands of the Fabry-Perot filter device.

Moreover, even with one type of gas, the Fabry-Perot filter device of the invention provides a plurality of transmission peaks in a plurality of wavelength bands, as shown in FIG. 14. For example, if the object being measured is carbon dioxide for which the gap "h" is set to be 2270 nm, transmission peaks occur in the vicinity of 2400 nm and 4250 nm. If the object is water vapor, for which the gap is set at 2590 nm, transmission peaks occur in the vicinity of 2700 nm and 4700 nm. If the object is reference light for which the gap "h" is set at 3100 nm, transmission peaks occur in the vicinity of 2200 nm and 3100 nm.

Figure 15:
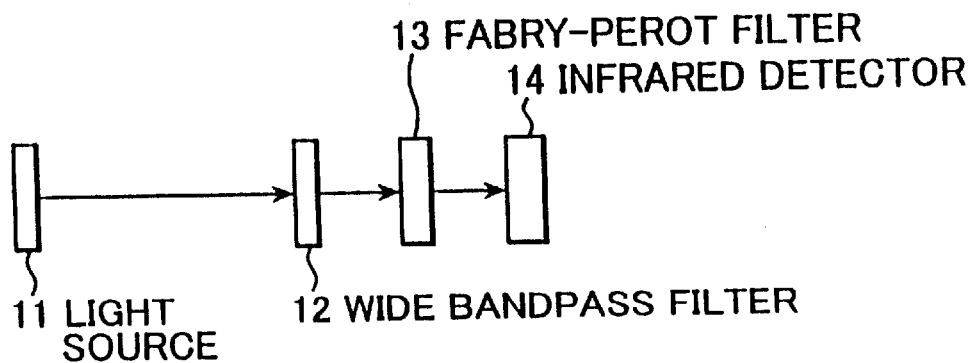
FIG. 15 is a schematic view depicting an infrared gas analyzer using the the Fabry-Perot filter device shown in FIGS. 13A–13C.

Accordingly, as shown in FIG. 15, a wide bandpass filter 12, which passes, for example, only the wavelength band of 2600 nm to 4500 nm and rejects from passage all other bands, can be located before an infrared detector 14 in the optical path, so that only one peak is selected for each width of the gap "h". That is, as shown in FIG. 14, only a band of wavelengths in the vicinity of 4250 nm is selected for carbon dioxide for which the gap "h" is set to 2270 nm. Also, similarly, only a band of wavelengths in the vicinity of 2700 nm is selected for water vapor for which the gap "h" is set to 2590 nm. Moreover, similarly, only a band of wavelengths in the vicinity of 3100 nm is selected for the reference light for which the gap "h" is set to 3100 nm. Hence, the Fabry-Perot filter device of the invention can be used to measure a plurality of gases utilizing the amount of absorption.

In the example of FIG. 15, the wide bandpass filter 12 is located between a light source 11 and a Fabry-Perot filter 13 in the optical path. Alternatively, wide bandpass filter 12 may be located between the Fabry-Perot filter 13 and infrared detector 14 in the optical path.

In the foregoing embodiment, only carbon dioxide and water vapor are discussed. However, other gas or gases can be measured with the invention. The design requirements for the Pabry-Perot filter are that the central wavelength occur within the range of from $\lambda 1$ to $\lambda 2$ and the free spectral range be greater than $\lambda 2 - \lambda 1$, assuming that the peak wavelengths of the infrared absorption of the two constituents are $\lambda 1$ (e.g. shorter wavelength) and $\lambda 2$ (e.g. longer wavelength). Accordingly, concentratidn measurement is also feasible for other constituent pairs, such as carbon dioxide and carbon monoxide, or nitrogen oxide and sulfur oxide, as examples.

Generally, the optical axes of the Fabry-Perot filter 13 and infrared detector 14 are positioned so as to be aligned with each other. In the case of the NDIR gas analyzers of the invention, the Fabry-Perot filter 13 and infrared detector 14 are two separate elements and may be difficult to align precisely. In such a case, instrument to instrument measurement error may occur depending on the alignment accuracy, and measures can be instituted to minimize error.

In order to increase the sensitivity of infrared detector 14 and to prevent the characteristics thereof from changing with time, infrared detector 14 can be encapsulated in a package and the package can be vacuum sealed or sealed with an inert gas therein.

In order to solve the foregoing problems, the Fabry-Perot filter of the invention is integrated with the infrared detector to form a wavelength selective infrared detector. A number of illustrative embodiments of the wavelength selective infrared detector are hereinafter discussed.

First Illustrative Embodiment of a Wavelength Selective Infrared Detector

Figure 16:
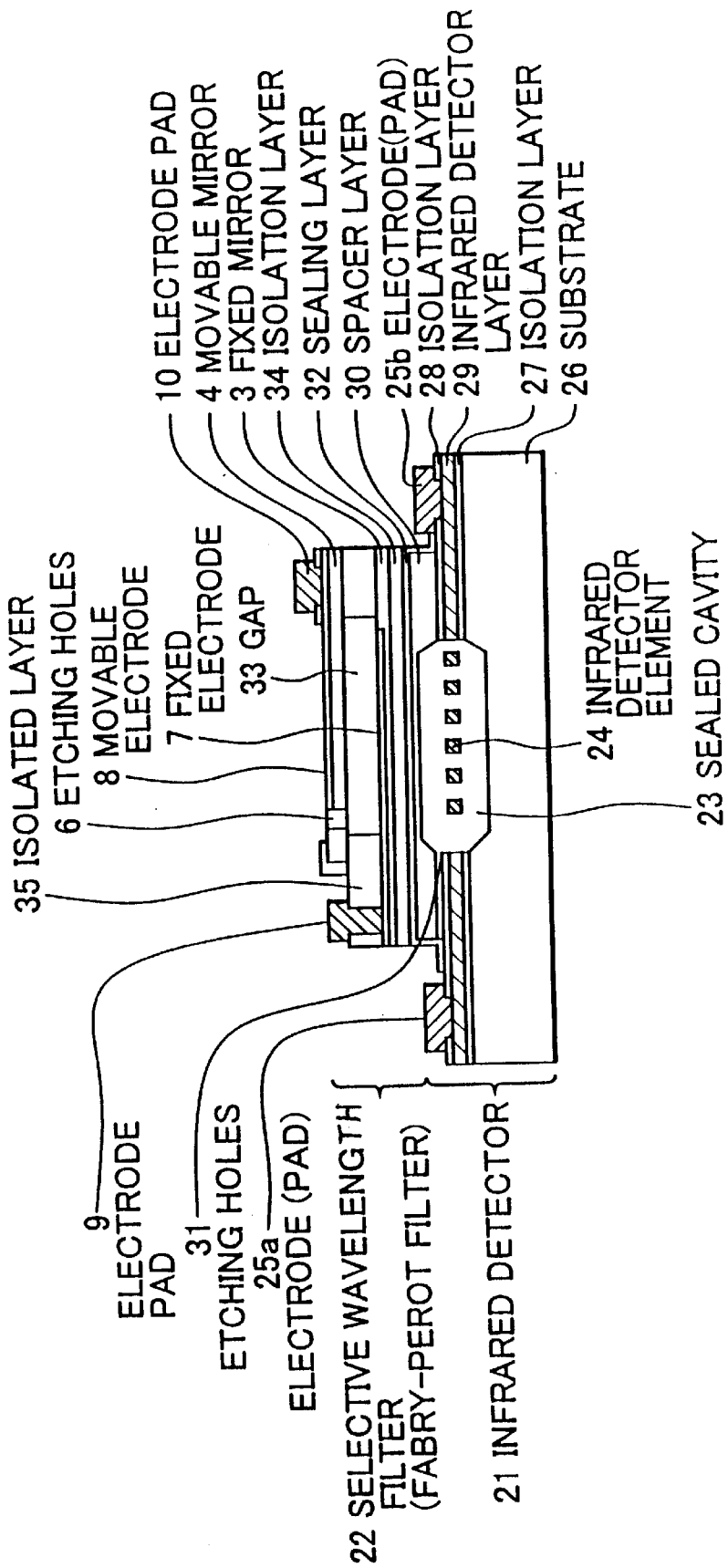
FIG. 16 is a cross-sectional view depicting a first illustrative embodiment of a wavelength selective infrared detector of the invention.

FIG. 16 shows a wavelength selective infrared, detector of the invention, wherein components identical to those in FIG. 10 have the same reference symbols and may be excluded from discussion hereat for sake of clarity. In FIG. 16, an infrared detector 21 is integrated with a wavelength selective filter 22 to form a wavelength selective infrared detector. The wavelength selective filter 22 may be a Fabry-Perot filter. Formed on a silicon substrate 26 are infrared detector 21, which is, for example, a bolometer wherein a sealed cavity 23, infrared detector elements 24 formed therein, and electrodes 25a and 25a wherein infrared detector 24 is supplied with power through the electrodes 25b, 25b.

The infrared detector elements 24 are formed by spirally etching conductive infrared detector layer 29 formed between isolation layer 27 and 28 comprising silicon oxide layers that are deposited on substrate 26. Infrared detector layer 29 comprises, for example, silicon with a high impurity concentration. A spacer layer 30 of silicon is formed on isolation layer 28. Then, etching holes 31 are formed between the spacer layer 30 and isolation layer 28. Then, sealed cavity 23 is formed by applying concentration difference etching through etching holes 31 to a portion of substrate 26 underlying the infrared detector elements 24, so that the elements are disposed within sealed cavity 23.

A sealing layer 32, of silicon, is formed on spacer layer 30 by means of epitaxial growth, for example, thereby closing the etching holes 31. In this process, sealed cavity 23 is filled with hydrogen that serves as a carrier gas during epitaxial growth. Sealed cavity 23 is then heat treated to drive the hydrogen gas out of the cavity so that a vacuum is formed therein. Hence, infrared detector elements 24 are vacuum sealed inside sealed cavity 23.

The wavelength selective filter 22 is a Fabry-Perot filter, which is similar to that shown in FIG. 10 with regard to the primary componets thereof, and comprises; a fixed mirror 3, a fixed electrode 7 formed on fixed mirror 3, and a movable electrode 8 formed on movable mirror 4. A gap 33 is formed between fixed mirror 3 and movable mirror 4 with the gap being varied by movement of the movable mirror 4 with respect to the fixed mirror 3.

As a first step in the process of fabricating wavelength selective filter 22, an isolation layer 34, made of silicon oxide, is formed on sealing layer 32, which serves as a substrate. Fixed mirror 3, which is made of, for example, polysilicon, is then formed on isolation layer 34. In the next step, a high concentration of impurity is doped onto the surface of fixed mirror 3, to form fixed electrode 7. Another isolation layer. 35 is formed on the fixed mirror 3, and the movable mirror 4, which comprises, for example, polysilicon, is formed on isolation layer 35 so as to be opposite the fixed mirror 3. On the surface of movable mirror 4, movable electrode 8, doped with a high concentration of impurity, is formed so as to be opposite fixed electrode 7.

After forming etching holes 6 in movable mirror 4, isolation layer 35 is etched through etching holes 6 so that a gap 33, whose width is equivalent to the thickness of the isolation layer 35, is formed between fixed mirror 3 and movable mirror 4. In this process, movable mirror 4 is connected through isolation layer 35 to fixed mirror 3, taking the form of a cantilever. Alternatively, a plurality of etching holes 6 may be formed in a circular array in movable mirror 4 to etch isolation layer 35, so that movable mirror 4 takes the form of a diaphragm. Electrode pad 9 is formed on fixed electrode 7 in contact therewith to enable electrode 7 to be electrically powered. Similarly, electrode pad 10 is formed on movable electrode 8 in contact therewith to enable electrode 8 to be supplied with power.

The operation of the wavelength selective infrared detector of FIG. 16 is as follows. When a potential difference is applied across fixed electrode 7 and movable electrode 8 through electrode pads 9 and 10, an electrostatic attractive force is produced therebetween. Thus, movable mirror 4 is displaced or moved toward fixed mirror 3, thereby to change the distance of gap 33. By varying the voltage thus supplied, it is possible to determine the width of gap 33 where infrared radiation with wavelength bands corresponding to the absorption bands of the gas being measured are caused to be transmitted through the wavelength selective filter. For example, assume that the width of gap 33 (which is the thickness of isolation layer 35 in a non-used state) in the non-powered state of the wavelength selective filter is 3.1 $\mu$m and that this initial state is the mode for measuring reference light. Then, the object to be measured can be switched to carbon dioxide by setting gap 33 to be approximately 2.27 $\mu$m. Similarly, the object can be switched to water vapor by setting the gap 33 to be approximately 2.59 $\mu$m.

Infrared radiation emitted from a light source, not shown, enters a sample cell, not shown, whereat gas being measured is supplied. The sample cell absorbs a specific band of wavelengths which is projected onto the movable mirror 4. Only the wavelength component corresponding to the width of gap 33 is caused to pass through fixed mirror 3 and enters infrared detector elements 24 within cavity 23 of the infrared detector 21. By detecting the amount of absorbed infrared radiation, the infrared detector elements 24 of the invention determine the concentration of the gas being measured.

Second Illustrative Embodiment of Wavelength Selective Infrared Detector

Figure 17A:
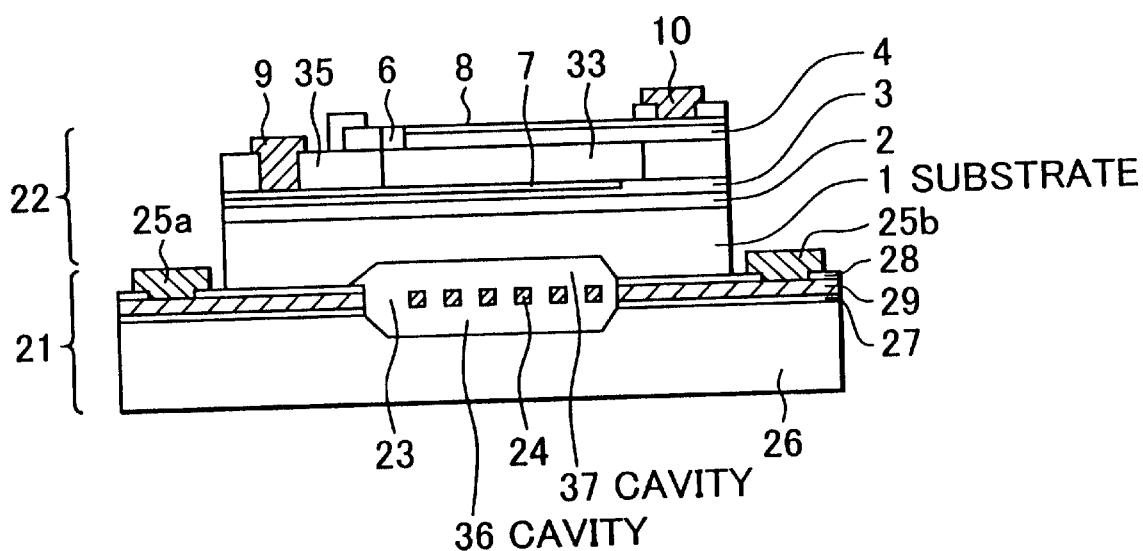
FIGS. 17A and 17B are cross-sectional views depicting a second illustrative embodiment of a wavelength selective infrared detector of the invention.
Figure 17B:
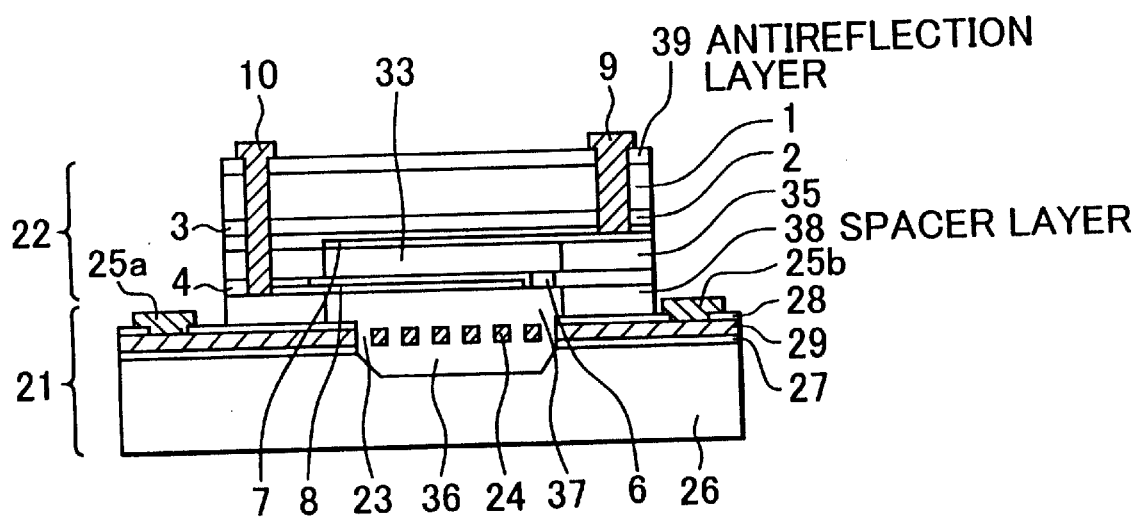

FIGS. 17A and 17B are cross-sectional views depicting a wavelength selective infrared detector of the invention, wherein components identical to those, of FIG. 16 have similar reference symbols and are not discussed hereat for sake of clarity. In FIG. 17A, an infrared detector 21, formed on a silicon substrate 26 which serves as a first substrate, and a waveform selective filter 22 formed on a silicon substrate 1, which serves as a second substrate, are joined together to form a wavelength selective infrared detector. Infrared detector 21 comprises, for example, a bolometer, wherein a cavity 36, serving as a sealed cavity, infrared detector elements 24 arranged in cavity 36, and electrodes 25a and 25b for powering the infrared detector elements. Infrared detector elements 24 are formed by spirally etching an infrared detector layer 29 formed between isolation layers 27 and 28 that are deposited on substrate 26. Then, cavity 36 is formed by etching a portion of substrate 26 underlying infrared detector elements 24 into the shape of a groove using a concentration difference method.

Wavelength selective filter 22 is a Fabry-Perot filter device comprising fixed mirror, movable mirror 4, fixed electrode 7 disposed on fixed mirror 3, and movable electrode 8 disposed on movable mirror 4. Another cavity 37 is formed on the backside of substrate 1. A sealed cavity 23 is formed by directly joining together substrate 26, whereon infrared detector 21 is formed, and substrate 1, whereon wavelength selective filter 22 is formed, in a vacuum or inert gas atmosphere, with cavities 36 and 37 being opposed to each other. Infrared detector elements 24 are disposed within sealed cavity 23. In this process, sealed cavity 23 is vacuum sealed or sealed with an inert gas therein.

In FIG. 17B, the wavelength selective infrared detector comprises wavelength selective filter 22, such as that shown in FIG. 17A, positioned upside down. Infrared detector 21 and wavelength selective filter 22 are joined together through a spacer layer 38 whereon cavity 37 is formed and cavity 23 is vacuum sealed or sealed with an inert gas therein.

Electrode pad 9 is formed to contact fixed electrode 7 so that power can be supplied to the fixed electrode 7 through an antireflection layer 39, deposited on substrate 1, through substrate 1 and through isolation layer 2. Similarly, electrode pad 10 is formed to contact movable electrode 8 so that power can be supplied thereto through antireflection layer 39, through substrate 1, through isblation layer 2, through fixed mirror 3, and through isolation layer 35.

Advantageously, the wavelength selective infrared detectors shown in FIGS. 16, 17A and 17B are fabricated using a semiconductor manufacturing process that allows for precision alignment. Accordingly, it is possible to align the infrared detector 21 and wavelength selective filter 22 with high precision, thereby reducing instrument to instrument error. Furthermore, advantageously, the wavelength selective infrared detectors are designed so that gap 33 can be varied by changing the voltage applied across the fixed and movable electrodes 7,8. Hence, there is no need to increase the number of filters even when a plurality of constituents in the gas being measured are included in the concentration measurement. Accordingly, with the invention, it is possible to reduce the size and cost of the infrared gas analyzers. Moreover, advantageously, in the process of manufacturing the infrared detector elements 24, sealed cavity 23 is either vacuum sealed or sealed with an inert gas therein. Hence, there is no need to use a separate sealing process, which enables further cost reduction.

Third Illustrative Embodiment of Wavelength Selective Infrared Detector

Figure 18:
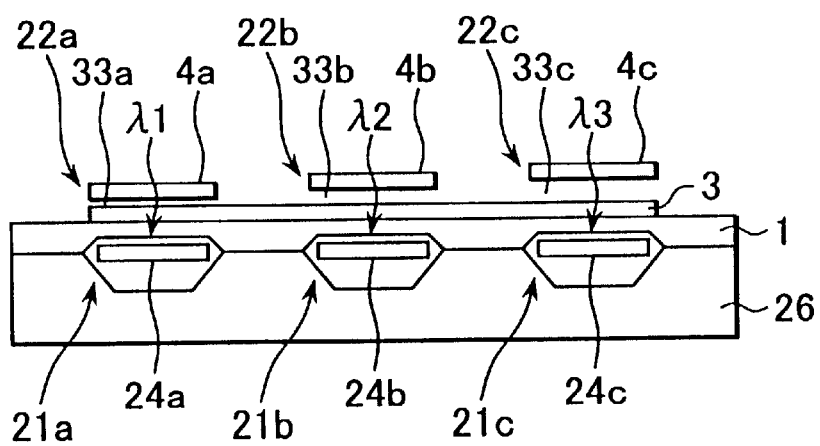
FIG. 18 is a cross-sectional view depicting a third illustrative embodiment of a wavelength selective infrared detector of the invention.

FIG. 18 shows another wavelength selective infrared detector of the invention, wherein the wavelength selective infrared detector comprises infrared detectors 21a, 21b, and 21c and wavelength selective filters 22a, 22b and 22c formed in a plurality of arrays. Infrared detectors 21a, 21b, and 21c are formed in parallel on substrate 26 similar to infrared detector 21 shown in FIGS. 17A, 17B. Similarly, wavelength selective filters 22a, 22b and 22c are formed in parallel on substrate 1 similar to wavelength selective filter 22 shown in FIGS. 17A, 17B. Also, similar to infrared detector shown in FIGS. 17A, 17B, infrared detector elements 24a, 24b and 24c are formed in infrared detectors 21a, 21b and 21c. Fixed mirror 3, located underneath wavelength selective filters 22a, 22b, and 22c, is formed so as to be common to the filters. Movable mirrors 4a, 4b, 4c are formed opposite fixed mirror 3.

In FIG. 18, assume that gaps 33a, 33b and 33c are formed between fixed mirror 3 and movable mirrors 4a, 4b, 4c so that the widths of the gaps differ from each other. Then, it is possible to fabricate wavelength selective filters 22a, 22b and 22c so that the respective filters will transmit only those bands of infrared radiation having the wavelengths $\lambda 1$, $\lambda 2$, $\lambda 3$ corresponding to the widths of the respective gaps.

Similar to the Fabry-Perot filter shown in FIGS. 17A, 17B, an array of wavelength selective infrared detectors can be formed by directly joining the substrates 1 and 26 together in a vacuum or inert gas atmosphere. Alternatively, similar to the wavelength selective infrared detector shown in FIG. 16, a plurality of infrared detectors and a plurality of wavelength selective filters may be formed on the same substrate. A plurality of wavelength selective infrared detectors may be arranged in an array on a horizontal plane, and the gaps of a plurality of wavelength selective filters may be formed so that the initial widths thereof differ from each other. Alternatively, the widths of a gap may be varied by changing an applied potential difference so that a plurality of constituents in a gas can be measured. In either case, it become possible to measure multicomponent gases.

Figure 19:
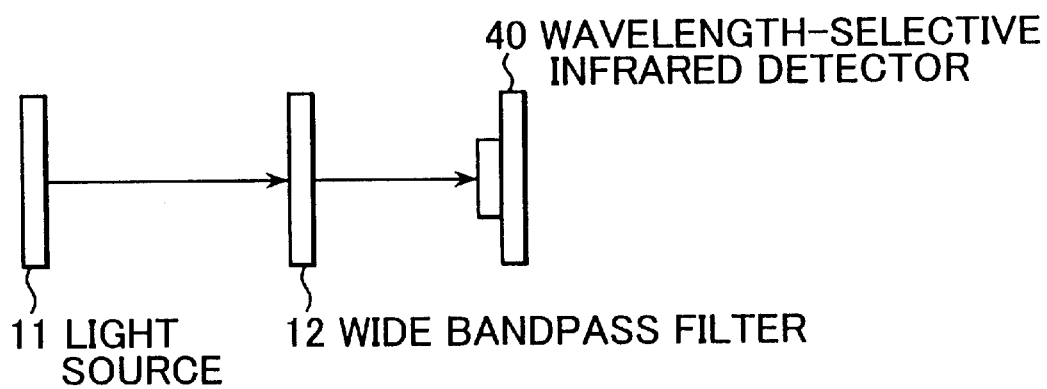
FIG. 19 is a schematic view depicting an infrared gas analyzer using the second and third illustrative embodiments of the wavelength selective infrared detector of the invention.

Even for one type of gas, the Fabry-Perot filter presents a plurality of transmission peaks in a plurality of wavelength bands, as shown in FIG. 14. Accordingly, as shown in FIG. 19, a wide bandpass filter 12 for transmitting, for example, only the wavelength band of 2600 to 4500 nm and rejecting all other bands, can be located in the optical path between light source 11 and wavelength selective infrared detector 40. That is to say, as shown in FIG. 14, only a band of wavelengths in the vicinity of 4250 nm is selected for carbon dioxide for which the gap is set to 2270 nm; and only a band of wavelengths in the vicinity of 2700 nm is selected for water vapor for which the gap is set to 2590 nm; and only a band of wavelengths in the vicinity of 3100 nm is selected for the reference light for which the gap is set to 3100 nm. Thus, the Fabry-Perot filter enables a plurality of gases to be measured by determining the amount of absorption.

Although the above description describes the infrared detector as being a bolometer, the invention is not so limited and other types of infrared detectors may be used, such as a vibrating infrared detector or quantum infrared detector.

The variable wavelength Fabry-Perot filter discussed above, may encounter one or more of the following problems.

Figure 20:
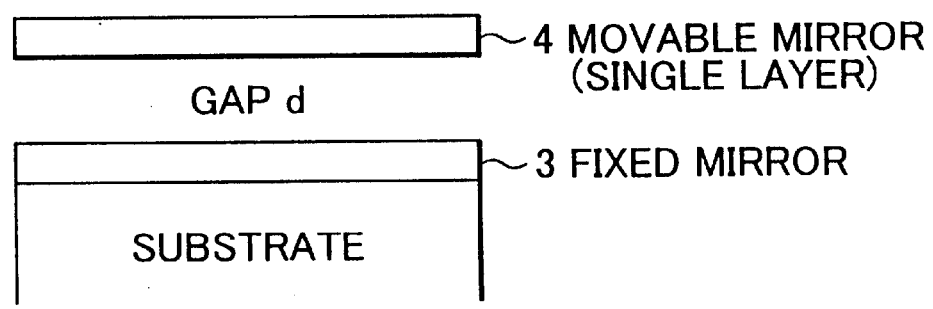
FIG. 20 is a schematic view depicting a Fabry-Perot filter.

(A) In the variable wavelength Fabry-Perot filter of the invention, the movable mirror 4 is formed using a single optical layer, as shown in FIG. 20. Fixed mirror 3 is formed on substrate 1. To be able to produce a single layer movable mirror 4, it is necessary to select layer forming material and conditions whereby the layer that forms movable mirror 4 will present tensile stress. For example, in order to form movable mirror 4 using polysilicon, it is necessary to form a layer or to dope the polysilicon with an impurity or impurities under the condition, wherein the polysilicon layer will present tensile stress. This method of forming layers may encounter one or more of the following problems.

(i) The tensile stress of a layer varies depending on the film forming conditions. Hence, stress control of layers becomes increasingly dependent on the film forming apparatus employed. For example, when forming a polysilicon film using an LPCVD system, the film has a tensile stress near 600° C. but has a compressive stress at a temperature below 570° C. or above 420° C. "LPCVD" means Low Pressure Chemical Vapor Deposition.

(ii) In order to use material having compressive stress, some structural measures, such as placing a frame around the film, must be used. In addition, it is difficult for a film with a large area to stand by itself.

(iii) As explained above in paragraphs (i) and (ii), the stress design tolerance of a self supporting film is comparatively narrow. This means that there is no choice but to select only a stress level that depends on the physical properties.

(B) In the variable Fabry-Perot filter device of the invention, the width of the gap between the fixed and movable mirrors is controlled by applying a voltage across the electrodes arranged opposite to each other and thereby producing a driving force. For this type of Fabry-Perot filter, an overvoltage exceeding a given rating might be applied across the electrodes due to static charges produced during operation. If any voltage above the rating is thus applied across the electrodes, the mirrors will approach too close to each other, or come into contact with each other, and hence, breakdown of dielectric will result, and short circuit current will flow through the mirrors. Consequently, the mirrors may break or become fused together, and the gap therebetween might not return to the original width even when the applied voltage is reset to zero. Alternatively, the mirrors may have a hysteresis characteristic. In other words, wavelength discrimination may become infeasible or the originally designed characteristics of applied voltage versus transmission wavelength, may become impaired.

(D) In the variable Fabry-Perot filter device of the invention, a sacrificial layer 41 (see FIG. 21) located between fixed mirror 3 and movable mirror 4 is etched through etching holes 6 using an etching liquid. This etching is discontinued when sacrificial layer 41 is etched into a gap of desired width. Thus, an air gap 42 is formed between the fixed and movable mirrors. This method of forming gaps may encounter one or more of the following problems.

(i) Due to variance of etching rate caused by the etching temperature, the service life of the etching liquid, or a difference in the concentration thereof, it is difficult to keep constant the size of the movable mirror or diaphragm 4 formed by etching sacrificial layer 41.

(ii) The gap is precisely position controlled by means of an equilibrium between the force of electrostatic attraction produced by voltage applied across the electrodes and the force of film tension. Accordingly, the applied voltage at which the desired gap is obtained differs from one movable mirror to another, as the size thereof also differs from one movable mirror to another. This means that calibration must be performed from one movable mirror to another.

(iii) Since etching is discontinued halfway, it is difficult to keep constant the microscopic shape of the edges of sacrificial layer 41. It is therefore likely that the applied voltage will vary depending on the shape.

(iv) Sacrificial layer 41 lies across almost the entire surface of substrate 1. If any pinhole occurs in the upper layer, a gap is formed at an unexpected location of the sacrificial layer 41 after etching process. Hence, a device failure may occur or dust may be produced.

The Fabry-perot filter device of the invention has solved the foregoing problems, wherein a movable mirror is fabricated using a multilayer optical thin film formed by laminating layers that show tensile stress (i.e. tensile stress layers) and layers that show compressive stress (i.e. compressive stress layers) or formed by laminating tensile stress layers that show different levels of tensile stress. Tensile stress and compressive stress layers can be formed using such materials as polysilicon, silicon oxide, or silicon nitride. Examples of possible combinations of tensile stress layers and compressive stress layers or of tensile stress layers only, include the following: (a) polysilicon compressive stress layer and silicon nitride tensile stress layer; (b) polysilicon compressive stress layer and silicon oxide tensile stress layer; (c) silicon oxide compressive stress layer and polysilicon tensile stress layer; (d) silicon nitride compressive stress layer and polysilicon tensile stress layer; (e) polysilicon tensile stress layer and silicon nitride tensile stress layer; and (f) polysilicon tensile stress layer and silicon oxide tensile stress layer.

According to the invention, as shown in FIG. 22, the multilayer optical thin film which forms the movable mirror is preferably a three layer optical thin film formed by laminating a high refractive index layer F1, a low refractive index layer F2 and another high refractive index layer F3 in the foregoing order. This structure permits the degree of film stress design to be heightened significantly. As specific examples of the three layer optical thin film, the film may be structured as follows.

(a) A three layer film consisting of (1) a high refractive index layer F1 presenting compressive stress, (2) a low refractive index layer F2 presenting tensile stress, and (3) a high refractive index layer F3 presenting compressive stress.

(b) A three layer film consisting of (1) a high refractive index layer F1 presenting tensile stress, (2) a low refractive index layer F2 presenting compressive stress, and (3) a high refractive index layer F3 presenting tensile stress.

(c) A three layer film consisting of (1) a high refractive index layer F1 presenting a low tensile stress level, (2) a low refractive index layer F2 presenting a high tensile stress level, and (3) a high refractive index layer F3 presenting a low tensile stress level.

(d) A three layer film consisting of (1) a high refractive index layer F1 presenting a high tensile stress level, (2) a low refractive index layer F2 presenting a low tensile stress level, and (3) a high refractive index layer F3 presenting a high tensile stress level.

Preferably, the multilayer optical thin film according to the invention should have an optical thickness of $\lambda/4$, wherein $\lambda$ is the wavelength. That is, the film should be a multilayer film equivalent to a single layer film having an optical film thickness of $\lambda/4$. At this point, the three layer film shown in FIG. 22 is optically equivalent to the single layer film having the optical thickness of $\lambda/4$ when the three layer film satisfies the following equation (2).

$$\lambda/4 = nd = n1d1 + n2d2 + n3d3 \qquad (2)$$

wherein $\lambda$ is the wavelength; n is the refractive index of a single layer film, d is the thickness of the single layer film, n1 is the refractive index of high refractive index layer F1, d1 is the thickness of the high refractive index layer F1, n2 is the refractive index of the low refractive index layer F2, and d2 is the thickness of the low refractive index layer F2, n3 is the refractive index of the high refractive index layer F3, and d3 is the thickness of the high refractive index layer F3.

Assuming that the membrane stress of each layer is $\delta1$, $\delta2$, and $\delta3$, in the case where a three layer film is used as the multilayer optical thin film, such as the movable mirror, then the membrane stress $\delta$ of the three layer film, as a whole, is approximately as shown by the below equation (3).

$$\delta = (\delta1 d1 + \delta2 d2 + \delta3 d3)/(d1 + d2 + d3) \qquad (3)$$

Assuming that, for example, the high refractive index layers F1 and F3 show compressive stress ($\delta1$ and $\delta3$) and the low refractive index layer F2 shows tensile stress ($\delta2$), then, by selecting the layer thicknesses of d1, d2 and d3, it is possible to design the membrane stress $\delta$ of the three layer film ranging from tensile stress to compressive stress.

Figure 23:
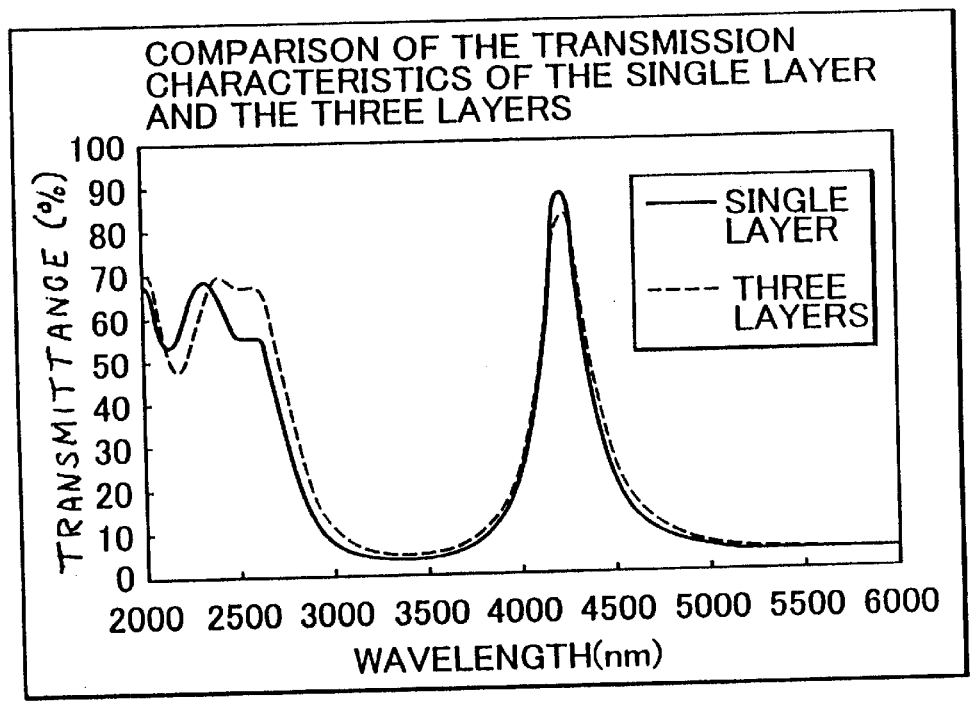
FIG. 23 is a graph depicting transmission characteristics of Fabry-perot filters, one of which uses a single layer and the other of which uses three layers for the movable mirror.

FIG. 23 shows transmission characteristics ($\lambda=4.25$ $\mu$m) for comparison between cases when a single layer film, made of polysilicon, is used for the movable mirror, and when a three layer film consisting of (1) a high refractive index layer F1 and presenting compressive stress and being of polysilicon, (2) a low refractive index layer F2 and presenting tensile stress and being of silicon nitride, and (3) a high refractive index layer F3 presenting compressive stress and being of polysilicon, is used for the movable mirror. The values for preparing the graph of the transmission characteristics shown in FIG. 23 are as follows:. Single layer film. n is 3.4245, d is 310 nm, and $\delta$ is −100 MPa; Three Layer film comprising (1) a high refractive index layer F1 which presents compressive stress and is made of polysilicon, n1 is 3.4245, d1 is 140 nm, and $\delta1$ is −100 MPa; (2) a low refractive index layer F2 presenting tensile stress and being of silicon nitride, n2 is 2.05, d2 is 50 nm and $\delta2$ is 1000 MPa; and (3) a high refractive index layer F3 presenting compressive stress and being of polysilicon, n3 is 3.4245, d3 is 140 nm, and $\delta3$ is −100 MPa. Optical film thickness, $n1d1 + n2d2 + n3d3 = \lambda/4 = 4.25/4$ $\mu$m. Membrane stress, tensile stress of 76 MPa.

Figure 24:
FIG. 24 is a schematic view explaining an example of a Fabry-Perot filter using a three layer movable mirror.
Figure 25:
FIG. 25 is a schematic view explaing an example of a Fabry-Perot filter using a single layer movable mirror.

As can be understood from FIG. 23, a Fabry-Perot filter, using a three layer movable mirror (see FIG. 24) and a Fabry-Perot filter, using a single layer movable mirror (see FIG. 25),share almost the same spectral characteristics. It can also be understood that even a single layer film may be incapable of being self-supporting and is subject to buckling due to compressive stress. On the other hand, a three layer structure will be self supporting and will not buckle. This is due to the fact that the overall membrane stress of the film turns the stress from compressive to tensile.

The invention is not limited to the foregoing examples of the Fabry-Perot filter device of the invention. For example, such applications, modifications, and extensions as described hereinbelow, are to be considered as part and parcel of the invention.

The invention is characterized in that an isolation layer is disposed between the electrodes so as to prevent the electrodes from being destroyed or fused when, for example, a voltage above the given rating thereof is applied across the electrodes. Accordingly, the invention is also applicable to electrostatic actuators, as a whole, wherein at least two electrodes are arranged opposite to each other and a voltage is applied thereto to produce a driving force. Moreover the invention is further applicable to optical devices as a whole, such as those which can switch between optical paths by use of a driving reflective mirror using an electrostatic actuator.

The structure of an electrostatic actuator is simple, since the basic components thereof are two or more electrodes. Hence, the invention encompasses a wide range of applications to electrostatic actuators in fields having marginal driving distances of $\mu m$ to 1 mm.

A self supporting movable mirror can be either upward convex or downward convex by changing the thickness balance between the topmost and bottommost of the three layers. An upward convex movable mirror, such as shown in FIG. 26, is advantageous in containment of light so that maximum transmission is improved.

The thickness of a multilayer film may be set at $\lambda/4$.

According to the invention, an isolation layer is located between fixed and movable electrodes and preferably on the fixed electrode. However, the isolation layer is not limited to such location. The isolation layer may be of, for example, silicon nitride or silicon oxide.

According to the invention, a gap is formed between the fixed and movable mirrors by first forming an artificial layer of predetermined shape and size between the fixed and movable mirrors, and then removing the layer completely by etching. For example, a sacrificial layer is formed to match the desired size of a movable mirror. Then, the movable mirror and other components are formed. Finally, the sacrificial layer is removed completely by wet etching through etching holes. Although dependent on accuracy of etching during the formation of the sacrificial layer, the size of the movable mirror becomes no longer dependent on etching accuracy when the sacrificial layer is etched away. Hence, it is possible to form a gap with higher precision. Although there is no restriction on the shape, the sacrificial layer preferably has a trapezoidal cross section, which is effective for relaxing stress concentration.

The multilayer film may be applied to other optical devices. In the area of micro-machining technology, in particular, it is possible to realize an electrostatic actuator of the invention in a convenient and economical manner.

Second Illustrative Embodiment of a Fabry-Perot Filter Device

FIGS. 27A and 27B show another Fabry-Perot filter device of the invention, wherein FIG. 27A represents the state of the Fabry-Perot filter device before etching of a sacrificial layer, whereas FIG. 27B shows the state thereof after etching. FIGS. 27A and 27B show a substrate 1, a fixed mirror 3, a movable mirror 4, etching holes 6, a fixed electrode 7, a movable electrode 8, an electrode pad 9, another electrode pad 10, a sacrificial layer 41, an air gap 42, an interlayer dielectric 43, an antireflection layer 44, a protection layer 45, an aperture 46, and an optical area 47.

Substrate 1 is made of a material for passing the given transmitted wavelength bands, for example, silicon, sapphire or germanium. Fixed mirror 3 is made of a single layer film or multilayer film having an optical thickness which is one quarter of the central wavelength $\lambda$ of the Fabry-Perot filter. One example of the multilayer film may be a film wherein high and low refractive index layers are formed of polysilicon and silicon oxide, respectively. Fixed electrode 7 is designed for electrostatic drive and is formed, for example, by doping the polysilicon of the fixed mirror with an impurity or impurities. The interlayer isolation layer 43 is designed to ensure isolation between fixed electrode 7 and movable electrode 8 and is made, for example, of silicon nitride.

Sacrificial layer 41 is a component used to form air gap 42 of the Fabry-Perot filter. By shaping and sizing the sacrificial layer so that a Fabry-Perot filter of desired size is fabricated as well as shaping the vertical cross-section of the layer to be a trapezoid, it is possible to secure relaxing of stress concentration. Sacrificial layer 41 is made of PSG or silicon oxide that can be removed using a fluoric acid etchant. "PSG" means Phospho-Silicate Glass.

Movable mirror 4 is a multilayer reflecting mirror that transmits a specific band of wavelengths by means of interference with fixed mirror 3. The movable mirror can be formed as a $Si/Si_3N_4/Si$ three layer mirror, for example, using silicon for the high refractive index top and bottom layers and silicon nitride for the low refractive index middle layer. Movable electrode 8 is intended for providing electrostatic drive and is formed, for example, by doping the silicon of movable mirror 4 with an impurity or impurities. Etching holes 6 are formed to allow an etching fluid, for etching the sacrificial layer 41, to enter therethrough. The etching holes 6 are formed at the center and along the periphery of the movable mirror, thereby allowing the etching fluid to be easily diffused, displaced and dried out.

Antireflection layer 44 is intended to increase the transmittance of light passing through the substrate in the case wherein the substrate of high refractive index is used. The antireflection layer 44 is made of a single layer or multiple layers having an optical thickness that allows the transmitted band of wavelengths to effectively be transmitted therethrough. For example, the Fabry-Perot filter device of the invention may use a combination of silicon and silicon oxide for substrate 1 and antireflection layer 41, respectively. Protection layer 45 is intended to prevent antireflection layer 44 from being attacked by an etching fluid when sacrificial layer 41 is etched, and is made of, for example, silicon nitride.

Aperture 46 is a layer for regulating the optical area 47 and is made of, for example, a film of metal such as gold. By etching aperture 46, optical area 47 is formed. Electrode pad 9 is a tapping pad of fixed electrode 7 and is made of , for example, a film of a metal, such as gold. Electrode pad 10 is a tapping pad of the movable electrode 8 and is made of, for example, a film of metal, such as gold. Air gap 42 is formed by etching the sacrificial layer 41 and serves as the distance of interference between the fixed and movable mirrors of the Fabry-Perot filter device. Optical area 47 is part of the Fabry-Perot filter where light is transmitted. Electrode pads 9 and 10 are located in a region external to the sacrificial layer 41.

In the foregoing embodiment, sacrificial layer 41 is removed by etching and is regulated with regard to size. Accordingly, the movable mirror or diaphragm 4 can be formed to be a specific size even when the rate of etching is varied. Hence, it is possible to realize a FabryPerot filter device of the invention having a variable gap of highly precise dimensions. Also, since the movable mirror 4 is multi-layered it is possible to broaden the stress design tolerance of a film comprising the movable mirror 4, as well as reduce the dependency of the film upon film forming apparatus.

Third Illustrative Embodiment of a Fabry-Perot Filter Device

Figure 28:
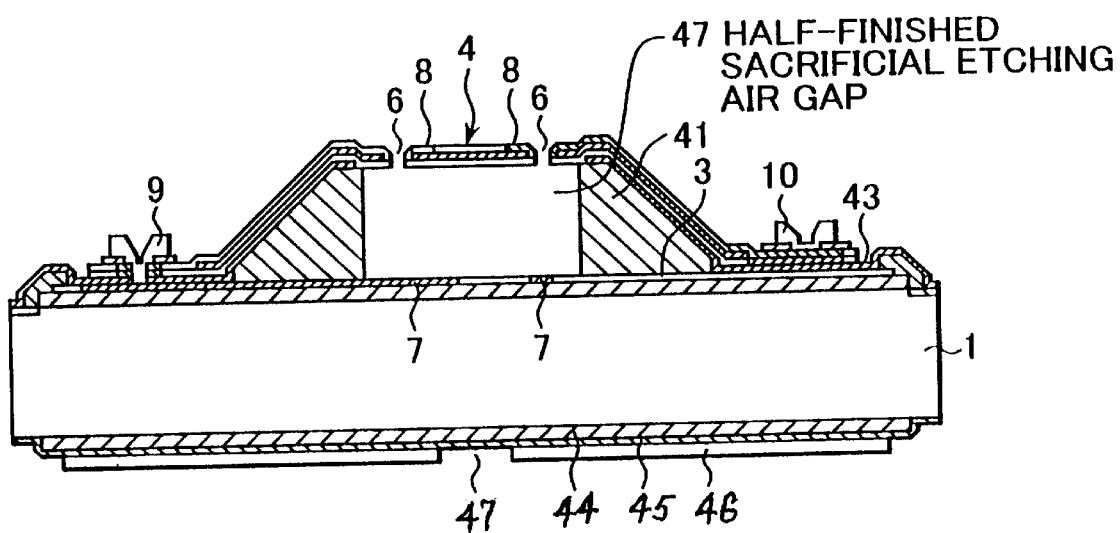
FIG. 28 is a cross-sectional view depicting a third illustrative embodiment of a Fabry-Perot filter device of the invention.

FIG. 28 shows another Fabry-Perot filter device of the invention, wherein components identical to those of FIGS. 27A and 27B have similar identification symbols and are not described hereat for sake of clarity. In addition, etching holes 6, which are otherwise disposed at the center of movable mirror 4, are omitted from the figure for sake of clarity of description.

The Fabry-Perot filter device of FIG. 28 has a halfway etched air gap 47 formed by controlling the etching time so that etching of sacrificial layer 41 is discontinued halfway of completion. In other words, air gap 42 is formed by discontinuing the etching of sacrificial layer 41 in the Second Illustrative Embodiment of the Fabry-Perot Filter Device, discussed above. Accordingly, it is possible to fabricate Fabry-Perot filters of different sizes with different mirror diameters in the described Second Illustrative Embodiment of a Fabry-Perot Filter Device. Accordingly, in the third embodiment of FIG. 28, it is possible to fabricate Fabry-Perot filter devices of different sizes using a single process. This is advantageous in that when the electrostatic drive voltage is changed due to the variance of stress in the movable mirror 4, such a change in voltage can be readily regulated by optimizing the etching time and thereby also optimizing the diameter of the moving mirror or diaphragm.

Fourth Illustrative Embodiment of a Fabry-Perot Filter Device

Figure 29:
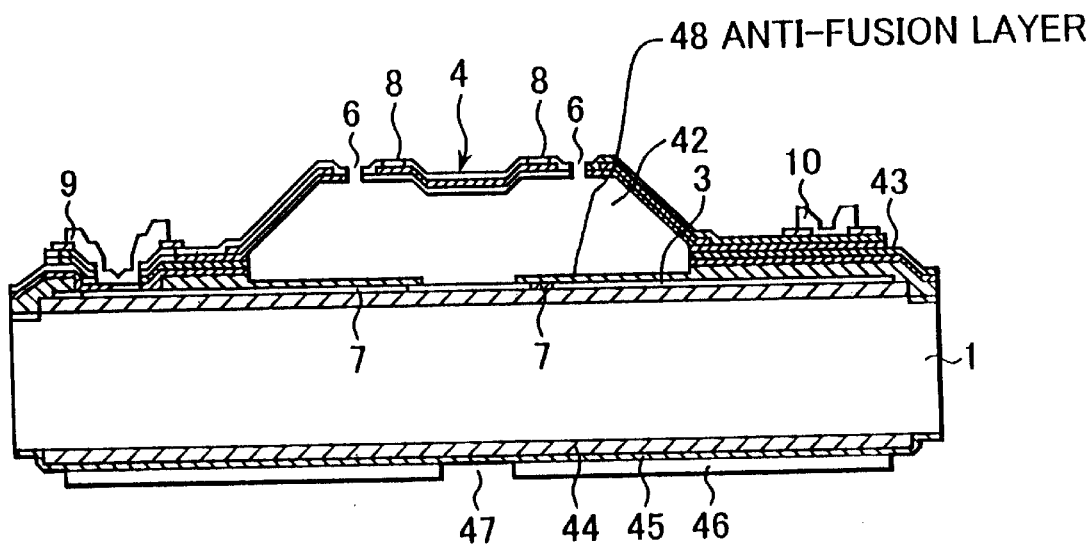
FIG. 29 is a cross-sectional view depicting a fourth illustrative embodiment of a Fabry-Perot filter device of the invention.

FIG. 29 shows a further Fabry-Perot filter device of the invention, wherein components identical to those shown in FIGS. 27A and 27B have similar identifying symbols and are not further discussed hereat for sake of clarity. In addition, etching holes 6, which are otherwise disposed at the center of the movable mirror 4, are omitted from the drawing to improve clarity and simplify the drawing. The embodiment of FIG. 29 comprises an antifusion (i.e. an isolation) layer 48 which prevents fixed electrode 7 from becoming fused with movable electrode 8 when the two electrodes come into contact with each other, and is disposed on the fixed mirror 7. The anti-fusion layer 48 is made of, for example, silicon nitride, and is adaptable to the filter embodiment of FIGS. 27A, 27B, and 28. In the application where the Fabry-Perot filter device is driven by applying an electrostatic drive voltage across electrode pads 9 and 10, no overcurrent will occur because of the anti-fusion layer 48, even in the case when a pull in phenomenon occurs wherein movable electrode 8 is attracted to fixed electrode 7 and comes into contact therewith. Consequently, it is possible to avoid having movable electrode 8 adhere to fixed electrode 7 due to fusion or for any other reason. The anti-fusion layer 48 does not adversely affect ejectrostatic drive even though it is located within the air gap 42.

Fifth Illustrative Embodiment of a Fabry-Perot Filter Device

Figure 30:
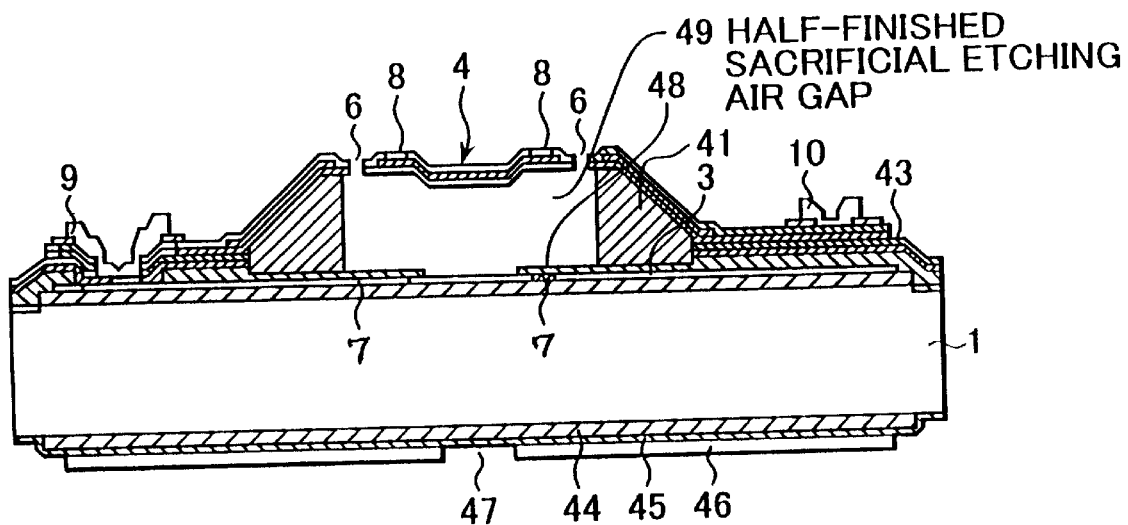
FIG. 30 is a cross-sectional view depicting a fifth illustrative embodiment of a Fabry-Perot filter device of the invention.

FIG. 30 shows a yet further Fabry-Perot filter device according to the invention, wherein components identical to those in FIGS. 27A and 27B are similarly identified by similar symbols and are not hereat described further for sake of clarity. In addition, etching holes 6, which are otherwise disposed at the center of movable mirror 4, are omitted for clarity of description. The filter device of FIG. 30 is fabricated so that etching of sacrificial layer 41 is discontinued halfway, as in the above embodiment of FIG. 28, so that a halfway etched air gap is formed. Accordingly, it is possible to fabricate Fabry-Perot filter devices having different sizes with different sized movable mirror diameters, in the filter configuration shown in embodiment of FIG. 29. The filter device of the embodiment of FIG. 30, therefore, has the same advantages as mentioned for the embodiment of FIG. 28, with regard to the halfway etched air gap 49. In addition, similar to the embodiment of FIG. 29, the Fabry-Perot filter device of FIG. 30 comprises an anti-fusion or isolation layer 48 that prevents fixed electrode 7 from becoming fused with movable electrode 8 when the two electrodes come into contact with each other. The anti-fusion layer 48 is disposed on fixed mirror 7. Therefore, the fifth illustrative embodiment of FIG. 30 has the same advantages as discussed with reference to the embodiment of FIG. 29 with regard to the anti-fusion layer 48.

Sixth Illustrative Embodiment of a Fabry-Perot Filter Device

Figure 31:
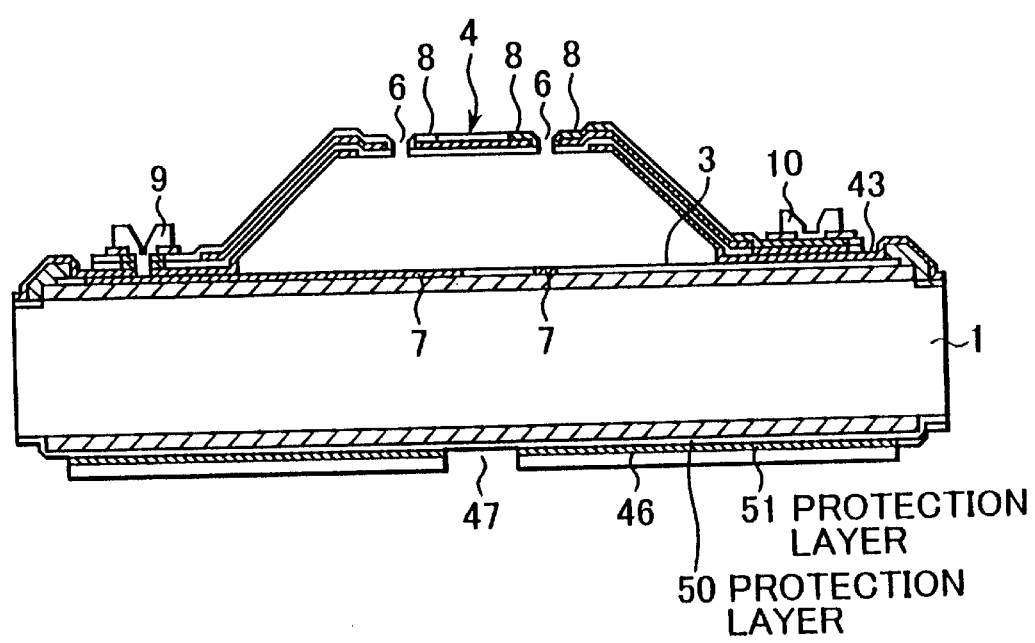
FIG. 31 is a cross-sectional view depicting a sixth illustrative embodiment of a Fabry-Perot filter device of the invention.

FIG. 31 shows a further Fabry-Perot filter device of the invention, wherein components identical to those shown in FIGS. 27A and 27B are identified with similar symbols and are not described further hereat for sake of clarity. In addition etching holes 6, which are otherwise disposed at the center of the movable mirror 4, are omitted for sake of simplicity.

The Fabry-Perot filter device of FIG. 31 is fabricated in such a manner that in the embodiment of FIGS. 27A and 27B, a backside protection layer, laminated with protection layers 50 and 51, is formed in place of protection layer 45. This backside protection layer is intended to protect the antireflection layer 44 when sacrificial layer 41 is etched. Upper protection layer 50 is made of, for example, polysilicon and the lower protection layer 51 is made of, for example silicon nitride. The backside protection layer in the embodiment of FIG. 31 is adaptable to any of the invention embodiments.

When metal film aperture 46 is formed in contact with protection layer 50, a residue of metal film may be produced when forming optical area 47. In contrast, aperture 46 does not come into contact with protection layer 50 when protection layer 51 is inserted between protection layer 50 and aperture 46. Hence, no metal film residue is produced in optical area 47, and, hence, transmittance of light is improved, when protection layer 51 is removed by wet etching during formation of optical area 47 and then protection layer 50 is also etched away.

If protection layer 45 is made of silicon nitride (e.g. in the embodiments of FIGS. 27A–30),the layer is also etched and the thickness thereof decreases as sacrificial layer 41 is etched with a fluoric acid etching fluid. This problem can be avoided, however, by inserting a layer of polysilicon which is highly resistant to fluoric acid, as protection layer 50. Hence, protection layer 50 serves as an etching stopper layer, thus, preventing antireflection layer 44 from being attacked by fluoric acid even when the silicon nitride protection layer 51 is etched. The polysilicon comprising the protection layer 50 can be easily removed by dry etching after artificial layer 41 is etched, with the aperture 46 serving as a mask.

By using a backside protection layer of polysilicon/silicon nitride structure , as described above, it is possible to protect antireflection layer 44 from attack by an etching fluid even for longer periods of etching time. In the filter device of the embodiment, it is also possible to completely remove part of the protection layer 45 occuring in optical area 47 and thereby improve transmittance of light, as compared with the embodiments of FIGS. 27A–30, wherein a small portion of protection layer 45 will unavoidably remain in optical area 47.

EFFECTS AND ADVANTAGES OF THE INVENTION

In one aspect of the invention, the width of the gap is made to be variable in three steps. Hence, it is possible to realize a Fabry-Perot filter device for selectively transmitting three wavelength bands of infrared radiation, including a wavelength band of reference light.

In another aspect, the infrared gas analyzer of the invention uses the Fabry-Perot filter device of the invention. Hence, it is possible to simultaneously measure the concentration of two constituents of the gas being measured, without having to increase the number of wavelength selective filters. Thus, it is also possible to reduce the size and the cost of infrared gas analyzers.

In a further aspect, the infrared gas analyzer uses the Fabry-Perot filter device of the invention and comprises a wide bandpass filter for transmitting only a specific band of wavelengths. Hence, it is possible to provide an infrared gas analyzer capable of measuring the concentrations of a plurality of gases by selecting only one peak for each width of the gap.

In a still further aspect, a wavelength selective filter and an infrared detector are integrated into one component, thereby providing accuracy of fabrication. Hence, it is possible to provide a small sized and low cost infrared gas analyzer.

In a further aspect, wavelength selective infrared detectors are arranged in arrays. Hence, it is possible to provide an infrared gas analyzer capable of measuring the concentrations of a multicomponent gas.

In another aspect, the infrared gas analyzer uses the wavelength selective infrared detector of the invention. Hence, it is possible to provide a small sized and low cost infrared gas analyzer.

In yet another aspect, the infrared gas analyzer uses the wavelength selective infrared detector of the invention and comprises a wide bandpass filter for transmitting only a specific band of wavelengths. Hence, it is possible to provide an infrared gas analyzer capable of measuring the concentrations of a plurality of gases by selecting only one peak for each width of the gap.

Moreover, the Fabry-Perot filter device of the invention is configured so as to broaden the stress design tolerance of a film comprising the movable mirror and to reduce the dependency of the film upon the film forming apparatus.

Furthermore, the Fabry-Perot filter device of the invention prevents mirrors from being destroyed or fused with each other, when, for example, an overvoltage occurs.

Also, the Fabry-Perot filter device of the invention employs a movable mirror of a constant size with high precision. Hence, the mirror to mirror variance is reduced of voltage at which desired width of gaps are obtained.

The foregoing description is illustrative of the principles of the invention. Numerous modifications and extensions thereof would be apparent to the worker skilled in the art. All such modifications and extensions are to be construed to be part and parcel of the invention.

What is claimed is:

1. A Fabry-Perot filter device comprising:
a fixed mirror;
a movably mirror arranged opposite to said fixed mirror with a gap formed therebetween; wherein
width of said gap is varied by displacing said movable mirror with respect to said fixed mirror; and wherein said movable mirror is formed using a multilayer optical thin film comprising at least one layer presenting tensile stress; wherein said thin film is a three layer optical thin film having a structure selected from the group consisting of the following structures (a)–(d):

(a) a structure wherein said thin film is produced by laminating a high refractive index layer presenting compressive stress, a low refractive index layer presenting tensile stress, and another high refractive index layer presenting compressive stress, in the foregoing order;

(b) a structure wherein said thin film is produced by laminating a high refractive index layer presenting tensile stress, a low refractive index layer presenting compressive stress, and another high refractive index layer presenting tensile stress, in the foregoing order;

(c) a structure wherein said thin film is produced by laminating a high refractive index layer presenting a low tensile stress, a low refractive index layer presenting a high tensile stress, and another high refractive index layer presenting a low tensile stress, in the foregoing order; and (d) a structure wherein said thin film is produced by laminating a high refractive index layer presenting a high tensile stresss, a low refractive index layer presenting a low tensile stress, and another high refractive index layer presenting a high tensile stress, in the foregoing order.

2. The device of claim 1, wherein thickness of said thin film is $\lambda/4$, wherein $\lambda$ is the wavelength.

3. The device of claim 1, wherein said movable mirror and said fixed mirror comprise silicon.

4. The device of claim 1, further comprising a fixed electrode formed on said fixed mirror; and a movable electrode formed on said movable mirror; and an isolation layer disposed between said fixed electrode and said movable electrode.

5. The device of claim 4, wherein said isolation layer is formed on said fixed electrode.

6. The device of claim 5, wherein said isolation layer is made of silicon nitride or silicon oxide.

7. The device of claim 4, wherein said movable mirror is displaced by applying a potential difference across said fixed electrode and said movable electrode so that a width of said gap is varied in at least three steps, whereby at least three wavelength bands of said infrared radiation are selectively transmitted through said Fabry-Perot filter device.

8. The device of claim 7, wherein said fixed electrode and said movable electrode comprise silicon with high impurity concentration.

9. The device of claim 1, wherein said fixed mirror is formed on a substrate, and wherein said gap is formed by depositing a sacrificial layer of predetermined shape and size between said fixed mirror and said movable mirror and then removing the sacrificial layer completely or partially by means of etching.

10. The device of claim 9, wherein a vertical cross section of said sacrificial layer is approximately a trapezoid and electrode pads are formed in a region outside of said sacrificial layer.

11. The device of claim 9, further comprising an antireflection layer formed on a backside of said substrate; and a metal aperture formed on said antireflective layer through a protection layer and having an optical area in part; wherein said sacrificial layer is first removed by etching and then a portion of said protection layer present in said optical area is removed.

12. The device of claim 9, further comprising etching holes formed at a center and along a periphery of said movable mirror in order to etch said sacrificial layer.

* * * * *